US012121596B2

(12) United States Patent
Achilefu et al.

(10) Patent No.: US 12,121,596 B2
(45) Date of Patent: *Oct. 22, 2024

(54) NEAR INFRARED FLUORESCENT DYES, FORMULATIONS AND RELATED METHODS

(71) Applicant: Washington University, St. Louis, MO (US)

(72) Inventors: Samuel Achilefu, St. Louis, MO (US); Rui Tang, St. Louis, MO (US); Duanwen Shen, St. Louis, MO (US); Avik Som, St. Louis, MO (US); Baogang Xu, St. Louis, MO (US); Gail Sudlow, St. Louis, MO (US); Christopher Egbulefu, St. Louis, MO (US); Partha Karmakar, St. Louis, MO (US); Kexian Liang, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/327,455

(22) Filed: Jun. 1, 2023

(65) Prior Publication Data

US 2023/0321283 A1 Oct. 12, 2023

Related U.S. Application Data

(63) Continuation of application No. 17/119,305, filed on Dec. 11, 2020, now Pat. No. 11,712,482.

(60) Provisional application No. 62/976,702, filed on Feb. 14, 2020, provisional application No. 62/947,974, filed on Dec. 13, 2019.

(51) Int. Cl.
*A61K 49/00* (2006.01)
*A61K 9/00* (2006.01)
*A61K 9/19* (2006.01)
*A61K 47/42* (2017.01)
*A61P 35/00* (2006.01)
*C09B 69/10* (2006.01)

(52) U.S. Cl.
CPC ........ *A61K 49/0034* (2013.01); *A61K 9/0019* (2013.01); *A61K 9/19* (2013.01); *A61K 47/42* (2013.01); *A61K 49/0056* (2013.01); *A61K 49/0089* (2013.01); *A61P 35/00* (2018.01); *C09B 69/105* (2013.01)

(58) Field of Classification Search
CPC .... A61K 49/0034; A61K 9/0019; A61K 9/19; A61K 47/42; A61K 49/0056; A61K 49/0089; A61P 35/00; C09B 69/105
See application file for complete search history.

(56) References Cited

U.S. PATENT DOCUMENTS

| | | |
|---|---|---|
| 4,987,021 A | 1/1991 | Kanno |
| 5,107,063 A | 4/1992 | West |
| 5,254,852 A | 10/1993 | Filipovich |
| 5,268,486 A | 12/1993 | Waggoner |
| 5,290,670 A | 3/1994 | Delprato |
| 5,453,505 A | 9/1995 | Lee |
| 5,506,705 A | 4/1996 | Yamamoto |
| 5,508,161 A | 4/1996 | Miyake |
| 5,518,934 A | 5/1996 | Forrest |
| 5,589,250 A | 12/1996 | Asai |
| 5,955,224 A | 9/1999 | Caspar |
| 5,959,705 A | 9/1999 | Fergason |
| 5,972,890 A | 10/1999 | Lees |
| 6,027,709 A | 2/2000 | Little |
| 6,217,848 B1 | 4/2001 | Achilefu |
| 6,272,374 B1 | 8/2001 | Flock |
| 6,358,920 B1 | 3/2002 | Blaschuk |
| 6,487,428 B1 | 11/2002 | Culver |
| 6,491,894 B1 | 12/2002 | Ruoslahti |
| 6,554,444 B2 | 4/2003 | Shimada |
| 6,585,660 B2 | 7/2003 | Dorando |
| 6,610,651 B1 | 8/2003 | Ruoslahti |
| 6,652,835 B1 | 11/2003 | Lauffer |
| 6,747,159 B2 | 6/2004 | Caputo |
| 6,804,549 B2 | 10/2004 | Hayashi |
| 6,944,493 B2 | 9/2005 | Alam |
| 7,134,994 B2 | 11/2006 | Alpert |
| 7,172,907 B2 | 2/2007 | Chen |
| 7,211,778 B1 | 5/2007 | Smith |

(Continued)

FOREIGN PATENT DOCUMENTS

| | | |
|---|---|---|
| JP | 06145539 | 5/1994 |
| WO | 1996017628 | 6/1996 |

(Continued)

OTHER PUBLICATIONS

Achilefu, S. et al., "Novel Receptor-Targeted Fluorescent Contrast Agents for In Vivo Tumor Imaging", Invest Radiol., 35(8):479-85, (2000).

Achilefu, S. et al., "Novel agent and system for imaging and therapy of arthritis", Washington University School of Medicine, 10 pages, (2021).

Achilefu, S. et al., "Synergistic Effects of Light-Emitting Probes and Peptides for Targeting and Monitoring Intergrin Expression", PNAS, 102(22):7976-81, (2005).

(Continued)

*Primary Examiner* — Robert S Cabral
(74) *Attorney, Agent, or Firm* — C A Schlecht; Midtown Intellectual Property, PC

(57) ABSTRACT

Provided herein is a pharmaceutical composition comprising an effective amount of cypate-Cyclo(Cys-Gly-Arg-Asp-Ser-Pro-Cys)-Lys-OH (LS301), cypate-Cyclo(Cys-Gly-Arg-Asp-Ser-Pro-Cys)-Tyr-OH (LS838) or pharmaceutically acceptable salts thereof, wherein each amino acid residue is independently in a D or L configuration; a divalent metal ion; and a pharmaceutically acceptable carrier. Further provided are lyophilized products comprising a dye-conjugate and m methods for identifying compromised and for binding phosphorylated annexin A2 (pANXA2) protein in a biological sample using a composition described herein.

37 Claims, No Drawings

(56) References Cited

U.S. PATENT DOCUMENTS

| | | |
|---|---|---|
| 7,547,721 B1 | 6/2009 | Miwa |
| 7,826,890 B1 | 11/2010 | Winchester, Jr. |
| 7,850,946 B2 | 12/2010 | Achilefu |
| 8,053,415 B2 | 11/2011 | Achilefu |
| 8,199,189 B2 | 6/2012 | Kagenow |
| 8,318,133 B2 | 11/2012 | Achilefu |
| 8,344,158 B2 | 1/2013 | Achilefu |
| 8,498,694 B2 | 7/2013 | McGuire, Jr. |
| 8,556,820 B2 | 10/2013 | Alpert |
| 8,562,537 B2 | 10/2013 | Alpert |
| 8,586,924 B2 | 11/2013 | Demos |
| 8,636,659 B2 | 1/2014 | Alpert |
| 9,687,567 B2 | 6/2017 | Frangioni |
| 10,230,943 B2 | 3/2019 | Achilefu |
| 10,652,527 B2 | 5/2020 | Achilefu |
| 10,806,804 B2 | 10/2020 | Achilefu |
| 10,904,518 B2 | 1/2021 | Achilefu |
| 11,310,485 B2 | 4/2022 | Achilefu |
| 11,413,359 B2 | 8/2022 | Achilefu |
| 11,712,482 B2 | 8/2023 | Achilefu |
| 11,765,340 B2 | 9/2023 | Achilefu |
| 2002/0028474 A1 | 3/2002 | Shibamura |
| 2002/0030163 A1 | 3/2002 | Zhang |
| 2002/0041898 A1 | 4/2002 | Unger |
| 2003/0105299 A1 | 6/2003 | Achilefu |
| 2004/0014981 A1 | 1/2004 | Lugade |
| 2004/0087778 A1 | 5/2004 | Feige |
| 2004/0215081 A1 | 10/2004 | Crane |
| 2006/0173351 A1 | 8/2006 | Marcotte |
| 2006/0173360 A1 | 8/2006 | Kalafut |
| 2007/0042398 A1 | 2/2007 | Peng |
| 2007/0084985 A1 | 4/2007 | Smith |
| 2008/0204361 A1 | 8/2008 | Scales |
| 2009/0028788 A1 | 1/2009 | Achilefu |
| 2009/0074672 A1 | 3/2009 | Faris |
| 2009/0093761 A1 | 4/2009 | Sliwa |
| 2009/0124792 A1 | 5/2009 | Achilefu |
| 2009/0137908 A1 | 5/2009 | Patwardhan |
| 2009/0214436 A1 | 8/2009 | Achilefu |
| 2009/0234225 A1 | 9/2009 | Martin |
| 2009/0242797 A1 | 10/2009 | Yazdanfar |
| 2009/0268983 A1 | 10/2009 | Stone |
| 2010/0110308 A1 | 5/2010 | Nicholson |
| 2010/0113940 A1 | 5/2010 | Sen |
| 2010/0215585 A1 | 8/2010 | Frangioni |
| 2010/0240988 A1 | 9/2010 | Varga |
| 2010/0323389 A1 | 12/2010 | Xu |
| 2011/0123450 A1 | 5/2011 | Achilefu |
| 2011/0213625 A1 | 9/2011 | Joao |
| 2011/0297815 A1 | 12/2011 | Tian |
| 2012/0026308 A1 | 2/2012 | Johnson |
| 2013/0116403 A1 | 5/2013 | Achilefu |
| 2013/0129835 A1 | 5/2013 | Pollock |
| 2013/0175430 A1 | 7/2013 | Cunningham |
| 2013/0317368 A1 | 11/2013 | Warren |
| 2014/0023700 A1 | 1/2014 | Knudsen |
| 2014/0039309 A1 | 2/2014 | Harris |
| 2014/0046291 A1 | 2/2014 | Harris |
| 2014/0121475 A1 | 5/2014 | Alpert |
| 2014/0152467 A1 | 6/2014 | Spencer |
| 2014/0155753 A1 | 6/2014 | McGuire, Jr. |
| 2014/0180032 A1 | 6/2014 | Millett |
| 2014/0180034 A1 | 6/2014 | Hoseit |
| 2014/0180056 A1 | 6/2014 | Hoseit |
| 2014/0180087 A1 | 6/2014 | Millett |
| 2014/0180135 A1 | 6/2014 | Hoseit |
| 2014/0180316 A1 | 6/2014 | Hoseit |
| 2014/0194704 A1 | 7/2014 | Millett |
| 2014/0200438 A1 | 7/2014 | Millett |
| 2014/0218210 A1 | 8/2014 | De Jong |
| 2014/0258743 A1 | 9/2014 | Nool |
| 2014/0275844 A1 | 9/2014 | Hoseit |
| 2014/0275950 A1 | 9/2014 | Hoseit |
| 2014/0276110 A1 | 9/2014 | Hoseit |
| 2015/0166791 A1 | 6/2015 | Achilefu |
| 2016/0206758 A1 | 7/2016 | Achilefu |
| 2016/0347727 A1 | 12/2016 | Frangioni |
| 2016/0370349 A1 | 12/2016 | Hoppin |
| 2018/0289842 A1 | 10/2018 | Achilefu |
| 2021/0177993 A1 | 6/2021 | Achilefu |
| 2022/0201274 A1 | 6/2022 | Achilefu |
| 2022/0378950 A1 | 12/2022 | Achilefu |
| 2023/0130831 A1 | 4/2023 | Achilefu |
| 2023/0388478 A1 | 11/2023 | Achilefu |

FOREIGN PATENT DOCUMENTS

| | | |
|---|---|---|
| WO | 1998022146 | 5/1998 |
| WO | 1998048838 | 11/1998 |
| WO | 1998048846 | 11/1998 |
| WO | 2000016810 | 3/2000 |
| WO | 2001005161 | 1/2001 |
| WO | 2001043781 | 6/2001 |
| WO | 2003074091 | 9/2003 |
| WO | 2004065491 | 8/2004 |
| WO | 2005000218 | 1/2005 |
| WO | 2006078914 | 7/2006 |
| WO | 2008017074 | 2/2008 |
| WO | 2011002209 | 1/2011 |
| WO | 2013112554 | 8/2013 |
| WO | 2016179350 | 11/2016 |
| WO | 2021119423 | 6/2021 |

OTHER PUBLICATIONS

Achilefu, S. et al., "Synthesis, In Vitro Receptor Binding, and In Vivo Evaluation of Fluorescein and Carbocyanine Peptide-Based Contrast Agents", J Med Chem., 45(10):2003-15, (2002).

Achilefu, S., "Lighting up Tumors with Receptor-Specific Optical Molecular Probes", Technol Cancer Res Treat., 3(4):393-409, (2004).

Agrapidis-Paloympis, L. et al., "The Effect of Solvents on the Ultraviolet Absorbance of Sunscreens", J Soc Cosmet Chem., 38:209-21, (1987).

Allman, R. et al., "In Vitro and in Vivo Effects of a Cyclic Peptide With Affinity for the alpha(nu)beta3 Integrin in Human Melanoma Cells", Eur J Cancer, 36(3):410-22, (2000).

Almutairi, K. et al., "The global prevalence of rheumatoid arthritis: a meta-analysis based on a systematic review", Rheumatol Int., 41(5):863-7, (2020).

Anonymous, "Guidelines for the management of rheumatoid arthritis. American College of Rheumatology Ad Hoc Committee on Clinical Guidelines", Arthritis Rheum., 39(5):713-22, (1996).

Arap, W. et al., "Cancer Treatment by Targeted Drug Delivery to Tumor Vasculature in a Mouse Model", Science, 279(5349):377-80, (1998).

Arnaout, M. et al., "Coming to Grips With Integrin Binding to Ligands", Curr Opin Biol., 14(5):641-51, (2002).

Arnaout, M., "Integrin Structure: New Twists and Turns in Dynamic Cell Adhesion", Immunol Rev., 186:125-40, (2002).

Bajpayee, A. et al., "Charge based intra-cartilage delivery of single dose dexamethasone using Avidin nano-carriers suppresses cytokine-induced catabolismlong term", Osteoarthritis Cartilage, 24(1):71-81, (2016).

Becker, A. et al., "Cyanine Dye Labeled Vasoactive Intestinal Peptide and Somaloslalin Analog for Optical Detection Jf Gastroenleropancreatic Tumors," Ann N Y Acad Sci., 291(1):275-8, (2000).

Becker, A. et al., "Receptor-Targeted Optical Imaging of Tumors With Near-Infrared Fluorescent Ligands", Nat Biotechnol., 19(4):327-31, (2001).

Becker, A. et al., "Transferrin-Mediated Tumor Delivery of Contrast Media for Optical Imaging and Magnetic Resonance Imaging", SPIE Confererence on Molecular Imaging: Reporters, Dyes, Markers and Instrumentation, 3600:142-50, (1999).

Berezin, M. et al., "Ratiometric Analysis of Fluorescence Lifetime for Probing Binding Sites in Albumin With Near-Infrared Fluorescent Molecular Probes", Photochem Photobiol., 83(6):1371-8, (2007).

Bharadwaj, A et al., "Annexin A2 heterotetramer: structure and function", Int J Mol Sci., 14(3):6259-305, (2013).

(56) References Cited

OTHER PUBLICATIONS

Bhatnagar, S. et al., "Oral and Subcutaneous Administration of a Near-Infrared Fluorescent Molecular Imaging Agent Detects Inflammation in a Mouse Model of Rheumatoid Arthritis", Sci Rep., 9(1):4661, (2019).
Bloch, S. et al., "Targeting Beta-3 Integrin Using a Linear Hexapeptide Labeled with a Near-Infrared Fluorescent Molecular Probe", Mol Pharm., 3(5):539-49, (2006).
Bloch, S. et al., "Whole-Body Fluorescence Lifetime Imaging of a Tumor-Targeted Near-Infrared Molecular Probe in Mice", J Biomed Opt., 10(5):054003, (2005).
Bouteiller, C. et al., "Novel Water-Soluble Near-Infrared Cyanine Dyes: Synthesis, Spectral Properties, and Use in the Preparation of Internally Quenched Fluorescent Probes", Bioconjugate Chem., 18(4):1303-17, (2007).
Braeckmans, K. et al., "Three-dimensional Fluorescence Recovery After Photobleaching With the Confocal Scanning Laser Microscope", Biophys J., 85(4):2240-52, (2003).
Braga, J. et al., "Intracellular Macromolecular Mobility Measured by Fluorescence Recovery After Photobleaching With Confocal Laser Scanning Microscopes", Mol Biol Cell., 15(10):4749-60, (2004).
Bremer, C. et al., "Imaging of Differential Protease Expression in Breast Cancers for Detection of Aggressive Tumor Phenotypes", Radiology, 222(3):814-8, (2002).
Brinkley, M., "A Brief Survey of Methods for Preparing Protein Conjugates With Dyes, Haptens, and Cross-Linking Reagents", Bioconjug Chem., 3(1):2-13, (1992).
Bugaj, J. et al., "Novel Fluorescent Contrast Agents for Optical Imaging of in Vivo Tumors Based on a Receptor-Targeted Dye-Peptide Conjugate Platform", J Biomed Opt., 6(2):122-33, (2001).
Chen, W et al., "Arthritis imaging using a near-infrared fluorescence folate-targeted probe", Arthritis Res Ther., 7(2):R310-7, (2005).
Chipon, B. et al., "Synthesis and Post-Synthetic Derivatization of a Cyanine-Based Amino Acid. Application to the Preparation of a Novel Water-Soluble NIR Dye", Tetrahedron Lett., 47(47):8279-84, (2006).
Cho, S. et al., "Indocyanine-Green for Fluorescence-Guided Surgery of Brain Tumors: Evidence, Techniques, and Practical Experience", Front Surg., 6(11):1-13, (2019).
Cooper, S., "Polyurethane Biomaterials", Abstract of Video Lecture; retrieved online at https://smartech.gatech.edu/handle/1853/42056, on Jul. 22, 2016; (2011).
De Jong, M. et al., "Comparison of 111 In-labeled Somatostatin Analogues for Tumor Scintigraphy and Radionuclide Therapy", Cancer Res., 58(3):437-41, (1998).
Definition of "Biomolecules," retrieved from https://www.thefreedictionary.com; 2 pages, (2014).
Deora, A. et al., "An annexin 2 phosphorylation switch mediates p11-dependent translocation of annexin 2 to the cell surface", J Biol Chem., 279(42):43411-8, (2004).
Deshpande, B. et al., "Number of Persons With Symptomatic Knee Osteoarthritis in the US: Impact of Race and Ethnicity, Age, Sex, and Obesity", Arthritis Care Res (Hoboken), 68(12):1743-50, (2016).
Enablement Decision Tree, accessed on Aug. 18, 2019.
EP Application No. 19152382.8; European Search Report, dated Sep. 18, 2019; 7 pages.
EP Patent Application No. 19152382.8; Extended European Search Report, dated Aug. 14, 2019; 7 pages.
Evans, C., "Catering to chondrocytes", Sci Transl Med., 10(469):eaav7043, (2018).
Fischer, T. et al., "Detection of rheumatoid arthritis using non-specific contrast enhanced fluorescence imaging", Acad Radiol., 17(3):375-81, (2010).
Fischer, T. et al., "Assessment of unspecific near-infrared dyes in laser-induced fluorescence imaging of experimental arthritis", Acad Radiol., 13(1):4-13, (2006).
Geiger, B. et al., "Cartilage-penetrating nanocarriers improve delivery and efficacy of growth factor treatment of osteoarthritis", Sci Transl Med., 10(469):eaat8800, (2018).

Glimm, A. et al., "Fluorescence optical imaging for treatment monitoring in patients with early and active rheumatoid arthritis in a 1-year follow-up period", Arthritis Res Ther., 21(1):209, (2019).
Gordon, G. et al., "Analysis of Simulated and Experimental Fluorescence Recovery After Photobleaching. Data for Two Diffusing Components", Biophys J., 68(3):766-78, (1995).
Grigor, C. et al., "Effect of a treatment strategy of tight control for rheumatoid arthritis (the TICORA study): a single-blind randomised controlled trial", Lancet., 364(9430):263-9, (2004).
Hansch, A. et al., "In vivo imaging of experimental arthritis with near-infrared fluorescence", Arthritis Rheum., 50(3):961-7, (2004).
Haraguchi, T., "Live Cell Imaging: Approaches for Studying Protein Dynamics in Living Cells," Cell Struct Funct., 27(5):333-4, (2002).
Haubner, R. et al., "Glycosylated RGD-containing Peptides: Tracer for Tumor Targeting and Angiogenesis Imaging With Improved Biokinetics", J Nucl Med., 42(2):326-36, (2001).
Haubner, R. et al., "Noninvasive Imaging of alpha(v)beta3 Integrin Expression Using 18F-labeled RGD-containing Glycopeptide and Positron Emission Tomography", Cancer Res., 61(5):1781-5, (2001).
Haubner, R. et al., "Radiolabeled alpha(v)beta3 Integrin Antagonists: A New Class of Tracers for Tumor Targeting", J Nucl Med., 40(6):1061-71, (1999).
Hilderbrand, S. et al., "Monofunctional Near-Infrared Fluorochromes for Imaging Applications," Bioconjug Chem., 16(5):1275-81, (2005).
Hunter, T. et al., "Prevalence of rheumatoid arthritis in the United States adult population in healthcare claims databases, 2004-2014", Rheumatol Int., 37(9):1551-7, (2017).
International Application No. PCT/US2004/017142; International Search Report and Written Opinion of the International Searching Authority, date of mailing Dec. 27, 2004; 6 pages.
International Application No. PCT/US2006/002056; International Preliminary Report on Patentability, date of issuance Jul. 24, 2007; 6 pages.
International Application No. PCT/US2006/002056; International Search Report and Written Opinion of the International Searching Authority, date of mailing May 24, 2006; 7 pages.
International Application No. PCT/US2013/022704; International Preliminary Report on Patentability, date of issuance Jul. 29, 2014; 5 pages.
International Application No. PCT/US2013/022704; International Search Report and Written Opinion of the International Searching Authority, date of mailing Apr. 18, 2013; 6 pages.
International Application No. PCT/US2016/030893; International Preliminary Report on Patentability, date of issuance Nov. 7, 2017; 9 pages.
International Application No. PCT/US2016/030893; International Search Report and Written Opinion of the International Searching Authority, date of mailing Sep. 9, 2016; 12 pages.
International Application No. PCT/US2020/064506; International Preliminary Report on Patentability, date of issuance Jun. 23, 2022; 7 pages.
International Application No. PCT/US2020/064506; International Search Report and Written Opinion of the International Searching Authority, date of mailing Apr. 22, 2021; 10 pages.
International Appliction No. PCT/US2006/002056; International Preliminary Report on Patentability, date of issuance Jul. 24, 2007; 7 pages.
Ito, S. et al., "Development of Fluorescence-Emitting Antibody Labeling Substance by Near-Infrared Ray Excitation", Bioorg Med Chem Lett., 5(22):2689-94, (1995).
Jain, R., "Barriers to Drug Delivery in Solid Tumors", Sci Am., 271(1):58-65, (1994).
Jamar, F. et al., "Scintigraphy using a technetium 99m-labelled anti-E-selectin Fab fragment in rheumatoid arthritis", Rheumatology (Oxford)., 41(1):53-61, (2002).
Janssen, M. et al., "Tumor Targeting With Radiolabeled alpha(v)beta(3) Integrin Binding Peptides in a Nude Mouse Model", Cancer Res., 62(21):6146-51, (2002).
Jones, J. et al., "Evaluation of a Tumor-Targeting, Near-Infrared Fluorescent Peptide for Early Detection and Endoscopic Resection of Polyps in a Rat Model of Colorectal Cancer", Mol Imaging, 17:1-9, (2018).

(56) References Cited

OTHER PUBLICATIONS

Kamradt, T. et al., "The role and clinical implications of G6PI in experimental models of rheumatoid arthritis", Arthritis Res Ther., 7(1):20-8, (2005).
Kisten, Y. et al., "Detection of clinically manifest and silent synovitis in the hands and wrists by fluorescence optical imaging", RMD Open., 1(1):e000106, (2015).
Krohn, M. et al., "Near-infrared Fluorescence Optical Imaging in Early Rheumatoid Arthritis: A Comparison to Magnetic Resonance Imaging and Ultrasonography", J Rheumatol., 42(7):1112-8, (2015).
Lee, H. et al., "Heptamethine Cyanine Dyes With a Robust C-C Bond at the Central Position of the Chromophore", J Org Chem., 71(20):7862-5, (2006).
Lee, H. et al., "Synthesis and Spectral Properties of Near-Infrared Aminophenyl-, Hydroxyphenyl-, and Phenyl-Substituted Heptamethine Cyanines", J Org Chem., 73(2):723-5, (2008).
Lenhard, J. et al., "Electrochemistry and Electronic Spectra of Cyanine Dye Radicals in Acetonitrile", J Phys Chem., 97(19):4916-25, (1993).
Leung, K.. "Cypate-Gly-Arg-Asp-Ser-Pro-Lys", Molecular Imaging and Contrast Agent Database (MICAD) [Internet]. Bethesda (MD): National Center for Biotechnology Information (US); 2004-13, (2005).
Lewis, J. et al., "Comparison of Four 64Cu-labeled Somatostatin Analogues in Vitro and in a Tumor-Bearing Rat Model: Evaluation of New Derivatives for Positron Emission Tomography Imaging and Targeted Radiotherapy", J Med Chem., 42(8):1341-7, (1999).
Lipsky, P. et al., "Infliximab and methotrexate in the treatment of rheumatoid arthritis. Anti-Tumor Necrosis Factor Trial in Rheumatoid Arthritis with Concomitant Therapy Study Group", N Engl J Med., 343(22):1594-602, (2000).
Liu, Y. et al., "Hands-Free, Wireless Goggles for Near-Infrared Fluorescence and Real-Time Image- Guided Surgery", Surgery, 149(5):689-98, (2011).
Licha, K. et al., "Hydrophilic Cyanine Dyes as Contrast Agents for Near-Infrared Tumor Imaging: Synthesis, Photophysical Properties and Spectroscopic in Vivo Characterization," Photochem Photobiol., 72(3):392-8, (2000).
Lukevits, É. et al., "Catalytic Synthesis and Reactions of Nitrogen Heterocycles (Review)", Chem Heterocyclic Compounds, 30(11-12):1284-307, (1994).
Meier, R. et al., "Indocyanine green-enhanced imaging of antigen-induced arthritis with an integrated optical imaging/radiography system", Arthritis Rheum., 62(8):2322-7, (2010).
Monach, P. et al., "The K/BxN arthritis model", Curr Protoc Immunol., Ch. 15, Un. 15.22, (2008).
Monach, P. et al., "The K/BxN mouse model of inflammatory arthritis: theory and practice", Methods Mol Med., 136:269-82, (2007).
Monti, S. et al., "Rheumatoid arthritis treatment: the earlier the better to prevent joint damage", RMD Open., 1(Suppl 1):e000057, (2015).
Mujumdar, R. et al., "Cyanine Dye Labeling Reagents: Sulfoindocyanine Succinimidyl Esters ", Bioconjug Chem., 4(2):105-11, (1993).
National Institute of Cancer—Understanding and Related Topics, accessed Aug. 18, 2019 at URL: https://www.cancer.gov/about-cancer/ understanding/what-is-cancer; 9 pages.
Ogul'chansky, T. et al., "Interactions of Cyanine Dyes With Nucleic Acids. XXIV. Aggregation of Monomethine Cyanine Dyes in Presence of DNA and Its Manifestation in Absorption and Fluorescence Spectra ," Spectrochim Acta A Mol Biomol Spectrosc., 57(7):1525-32, (2001).
Otero, M. et al., "Cells of the synovium in rheumatoid arthritis. Chondrocytes", Arthritis Res Ther., 9(5):220, (2007).
Patonay, G. et al., "Near-Infrared Fluorogenic Labels: New Approach to an Old Problem", Anal Chem., 63(6):321A-7A, (1991).
Pretsch, E. et al., "UV-Absorption of alpha.beta-Unsaturated Carbonyl Compounds; UV-Absorption of Dienes and Polyenes; UV-Absorption of Aromatic Carbonyl Compounds; UV-Absorption of Aromatic Compounds," Spectral Data or Structure Determination of Organic Compounds, Chemical Laboratory Practice, 2nd ed., pp. U20, U25, U30, U35, U40, U45, U50, (1989).
Qin, R., "Intraoperative Fluorescence Surgical Goggle", Knowledge Bank osu.edu, 9 pages, (2009).
Registry No. 70446-35-4, 1 page, (1984).
Roland, J et al., "Optical Versus Video See-Through Head-Mounted Displays in Medical Visualization", Presence, 9(3):287-309, (2000).
Romão, V. et al., "Major Challenges in Rheumatology: Will We Ever Treat Smarter, Instead of Just Harder?", Front Med (Lausanne), 6:144, (2019).
Rosner, B., "Fundamentals of Biostatistics", 7th ed. Boston: Brooks/Cole; (2011).
SALOMON-ESCOTO, K. et al., "The 'Treat to Target' Approach to Rheumatoid Arthritis". Rheum Dis Clin North Am., 45(4):487-504, (2019).
Schäfer, V. et al., "Quantitative assessment of synovitis in patients with rheumatoid arthritis using fluorescence optical imaging.", Arthritis Res Ther., 15(5):R124, (2013).
Shen, D. et al., "Selective Imaging of Solid Tumours Via the Calcium-Dependent High-Affinity Binding of a Cyclic Octapeptide to Phosphorylated Annexin A2", Nat Biomed Engin., 4(3):298-313, (2020).
SIGMA—@ sodium dodecyl sulfate (Production Information), Product No. L 3771, retrieved from https://www.sigmaaldrich.com/content/dam/sigma-aldrich/docs/Sigma/Product_Information_Sheel/2/13771 pis.pdf; 1 page, (revised Oct. 2002).
Sivolapenko, G. et al., "Imaging of Metastatic Melanoma Utilising a technetium-99m Labelled RGD-containing Synthetic Peptide ", Eur J Nucl Med, 25(10):1383-9, (1998).
Smolen, J et al., "EULAR recommendations for the management of rheumatoid arthritis with synthetic and biological disease-modifying antirheumatic drugs: 2016 update", Ann Rheum Dis., 76(6):960-77, (2017).
Smolen, J. et al., "Tocilizumab inhibits progression of joint damage in rheumatoid arthritis irrespective of its anti-inflammatory effects: disassociation of the link between inflammation and destruction", Ann Rheum Dis., 71(5):687-93, (2012).
Song, C. et al., "Regulation of inflammatory response in human chondrocytes by lentiviral mediated RNA interference against S100A10", Inflamm Res., 61(11):1219-27, (2012).
Troyan, S et al., "The FLARE Intraoperative Near-Infrared Fluorescence Imaging System: A First-in-Human Clinical Trial in Breast Cancer Sentinel Lymph Node Mapping", Ann Surg Oncol., 16(10):2943-52, (2009).
Tsen, S. et al., "Non-invasive monitoring of arthritis treatment response via targeting of tyrosine-phosphorylated annexin A2 in chondrocytes", Arthritis Res Ther., 23(1):265, (2021).
Tseng, C. et al., "Dual Role of Chondrocytes in Rheumatoid Arthritis: The Chicken and the Egg", Int J Mol Sci., 21(3):1071, (2020).
U.S. Appl. No. 10/559,000; Notice of Allowance, dated Aug. 2, 2010; 4 pages.
U.S. Appl. No. 10/559,000; Final Office Action, dated Oct. 14, 2009; 10 pages.
U.S. Appl. No. 10/559,000; Non-Final Office Action, dated Mar. 3, 2010; 4 pages.
U.S. Appl. No. 10/559,000; Non-Final Office Action, dated Mar. 10, 2009; 8 pages.
U.S. Appl. No. 12/192,480; Final Office Action, dated Dec. 13, 2011; 9 pages.
U.S. Appl. No. 12/192,480; Non-Final Office Action, dated Aug. 19, 2011; 10 pages.
U.S. Appl. No. 12/192,480; Non-Final Office Action, dated Mar. 7, 2011; 13 pages.
U.S. Appl. No. 12/192,480; Non-Final Office Action, dated May 1, 2012; 12 pages.
U.S. Appl. No. 12/192,480; Notice of Allowance, dated Sep. 4, 2012; 7 pages.
U.S. Appl. No. 12/370,758; Final Office Action, dated May 25, 2012; 12 pages.
U.S. Appl. No. 12/370,758; Non-Final Office Action, dated Aug. 28, 2014; 10 pages.

(56) References Cited

OTHER PUBLICATIONS

U.S. Appl. No. 12/370,758; Non-Final Office Action, dated Dec. 4, 2015; 10 pages.
U.S. Appl. No. 12/370,758; Non-Final Office Action, dated Sep. 30, 2011; 12 pages.
U.S. Appl. No. 12/938,086; Non-Final Office Action, dated Apr. 3, 2012; 8 pages.
U.S. Appl. No. 12/938,086; Notice of Allowance, dated Jul. 23, 2012; 7 pages.
U.S. Appl. No. 13/712,317; Final Office Action, dated Jul. 11, 2014; 12 pages.
U.S. Appl. No. 13/712,317; Non-Final Office Action, dated Jan. 17, 2014; 15 pages.
U.S. Appl. No. 13/712,317; Non-Final Office Action, dated May 21, 2015;14 pages.
U.S. Appl. No. 14/624,532; Final Office Action, dated Dec. 1, 2017; 8 pages.
U.S. Appl. No. 14/624,532; Final Office Action, dated Nov. 4, 2016; 11 pages.
U.S. Appl. No. 14/624,532; Non-Final Office Action, dated Jul. 5, 2017; 9 pages.
U.S. Appl. No. 14/624,532; Non-Final Office Action, dated Jul. 15, 2016; 12 pages.
U.S. Appl. No. 15/090,055; Final Office Action, dated Aug. 9, 2019; 9 pages.
U.S. Appl. No. 15/090,055; Final Office Action, dated Jul. 24, 2017; 16 pages.
U.S. Appl. No. 15/090,055; Non-Final Office Action, dated Apr. 6, 2017; 17 pages.
U.S. Appl. No. 15/090,055; Non-Final Office Action, dated Nov. 7, 2018; 10 pages.
U.S. Appl. No. 15/572,087; Final Office Action, dated Jan. 17, 2020; 25 pages.
U.S. Appl. No. 15/572,087; Notice of Allowance, dated Jun. 10, 2020; 11 pages.
U.S. Appl. No. 16/169,071; Applicant-Initiated Interview Summary, dated Jul. 2, 2020; 3 pages.
U.S. Appl. No. 16/169,071; Applicant-Initiated Interview Summary, dated Sep. 18, 2020; 2 pgaes.
U.S. Appl. No. 16/169,071; Corrected Notice of Allowability, dated Dec. 17, 2020; 4 pages.
U.S. Appl. No. 16/169,071; Final Office Action, dated Jun. 26, 2020; 13 pages.
U.S. Appl. No. 16/169,071; Notice of Allowance, dated Sep. 28, 2020; 8 pages.
U.S. Appl. No. 16/189,551; Notice of Allowance, dated Jan. 20, 2020; 5 pages.
U.S. Appl. No. 17/017,135; Examiner-Initiated Interview Summary, dated May 6, 2022; 1 page.
U.S. Appl. No. 17/017,135; Non-Final Office Action, dated Dec. 22, 2021; 25 pages.
U.S. Appl. No. 17/017,135; Notice of Allowance, dated May 12, 2022; 10 pages.
U.S. Appl. No. 17/119,305; Notice of Allowance, dated Mar. 3, 2023; 11 pages.
U.S. Appl. No. 17/122,848; Non-Final Office Action, dated Aug. 11, 2021; 22 pages.
U.S. Appl. No. 17/122,848; Notice of Allowance, dated Dec. 15, 2021; 5 pages.
U.S. Appl. No. 17/689,339; Non-Final Office Action, dated Jan. 25, 2023; 25 pages.
U.S. Appl. No. 17/689,339; Notice of Allowance, dated May 15, 2023; 11 pages.
Van Hagen, P. et al., "Evaluation of a Radiolabelled Cyclic DTPA-RGD Analogue for Tumour Imaging and Radionuclide Therapy", Int J Cancer, 90(4): 186-98, (2000).
Viitanen, R. et al., "First-in-Humans Study of 68Ga-DOTA-Siglec-9, a PET Ligand Targeting Vascular Adhesion Protein 1", J Nucl Med., 62(4):577-83, (2021).
Vina, E. et al., "Epidemiology of osteoarthritis: literature update", Curr Opin Rheumatol., 30(2):160-7, (2018).
Wakefield, R. et al., "The value of sonography in the detection of bone erosions in patients with rheumatoid arthritis: a comparison with conventional radiography", Arthritis Rheum., 43(12):2762-70, (2000).
Wang, H. et al., "Indocyanine green-incorporating nanoparticles for cancer theranostics", Theranostics, 8(5):1227-42, (2018).
Weissleder, R., "A Clearer Vision for in Vivo Imaging ," Nat Biotechnol., 19(4):316-7, (2001).
Werle, M. et al., "Strategies to improve plasma half life time of peptide and protein drugs", Amino Acids, 30(4):351-67, (2006).
Werner, S. et al., "Indocyanine green-enhanced fluorescence optical imaging in patients with early and very early arthritis: a comparative study with magnetic resonance imaging", Arthritis Rheum., 65(12):3036-44, (2013).
Werner, S. et al., "Inflammation assessment in patients with arthritis using a novel in vivo fluorescence optical imaging technology", Ann Rheum Dis., 71(4):504-10, (2012).
Wijbrandts, C. et al., "Prediction of Response to Targeted Treatment in Rheumatoid Arthritis", Mayo Clin Proc., 92(7):1129-43, (2017).
Yang, L. et al., "Hands-Free, Wireless Goggles for Near-Infrared Fluorescence and Real-Time Image-Guided Surgery", Surgery, 149(5):689-98, (2011).
Ye, Y. et al., "Design, Synthesis, and Evaluation of Near Infrared Fluorescent Multimeric RGD Peptides for Targeting Tumors ", J Med Chem., 49(7):2268-75, (2006).
Ye, Y. et al., "Integrin Targeting for Tumor Optical Imaging", Theranostics, 1:102-26, (2011).
Ye, Y. et al., "Multivalent Carbocyanine Molecular Probes: Synthesis and Applications", Bioconjug Chem, 16(1):51-61, (2005).
Ye, Y. et al., "Novel Near-Infrared Fluorescent Integrin-Targeted DFO Analogue", Bioconjug Chem., 19(1):225-34, (2008).
Ye, Y. et al., "Polyvalent Carbocyanine Molecular Beacons for Molecular Recognitions", J Am Chern, 126(25):7740-1, (2004).
Yi, J et al., "The Annexin a2 Promotes Development in Arthritis through Neovascularization by Amplification Hedgehog Pathway", PLoS One, 11(3):e0150363, (2016).
Zhang, Z. et al., "Monomolecular Multimodal Fluorescence-Radioisotope Imaging Agents", Bioconjug Chem., 16(5):1232-9, (2005).
Zhao, W. et al., "The discoidin domain receptor 2/annexin A2/matrix metalloproteinase 13 loop promotes joint destruction in arthritis through promoting migration and invasion of fibroblast-like synoviocytes", Arthritis Rheumatol., 66(9):2355-67, (2014).
Zheng, L. et al., "Tyrosine 23 phosphorylation-dependent cell-surface localization of annexin A2 is required for invasion and metastases of pancreatic cancer", PLoS One., 6(4):e19390, (2011).
Zhou, H. et al., "Alphavbeta3-targeted nanotherapy suppresses inflammatory arthritis in mice", Faseb J., 23(9):2978-85, (2009).
Zhou, H. et al., "Synergistic effect of antiangiogenic nanotherapy combined with methotrexate in the treatment of experimental inflammatory arthritis", Nanomedicine (Lond)., 5(7):1065-74, (2010).

NEAR INFRARED FLUORESCENT DYES, FORMULATIONS AND RELATED METHODS

CROSS-REFERENCE

This application claims the benefit of the filing date as a continuation of the U.S. patent application Ser. No. 17/119,305, filed on Dec. 11, 2020, now allowed, which claims the benefit of priority of U.S. Provisional Patent Application Ser. No. 62/947,974 filed Dec. 13, 2019, and also claims the benefit of priority of U.S. Provisional Patent Application Ser. No. 62/976,702 filed Feb. 14, 2020, the disclosures of which are each incorporated by reference in their entireties for all purposes.

GOVERNMENT LICENSE RIGHTS

This invention was made with government support under Award No. R01 CA171651 awarded by the National Institutes of Health. The government has certain rights in the invention.

TECHNICAL FIELD

The present disclosure provides pharmaceutical formulations comprising LS301 or LS838, fluorescent dye-cyclic polypeptide conjugates (dye-conjugates). The formulations herein are suitable for systemic delivery, such as intravenous injection, topical application, and oral gavage.

BACKGROUND

Elevated chronic inflammatory milieu, metabolic aberrations, and genetic mutations drive cancer cells' dynamic adaptation toward their survival, proliferation, and metastasis. Accompanying alterations in cellular processes produce heterogeneous populations of cancer subtypes and distorted stroma characterized by diverse cancer biomarkers. Progress in cancer targeted therapies and imaging relies on effectively and selectively delivering molecules to overexpressed cell surface proteins. Yet, the evolving landscape of tumor survival mechanisms frustrates developing molecularly targeted drugs and imaging agents for each cancer type.

One such cell surface protein is annexin A2 (ANXA2), a member of the annexin family of calcium-dependent phospholipid-binding proteins. ANXA2 exhibits cancer-associated posttranslational modifications (PTMs). It is upregulated in many cancers, including breast, colon, liver, pancreatic, and brain tumors, suggesting a role in tumor proliferation, angiogenesis, invasion, and metastasis. Phosphorylation of ANXA2 at tyrosine 23 (pANXA2) modulates ANXA2 tetramer formation and is a prerequisite for its translocation to the plasma membrane. This PTM occurs in response to growth factor signaling and promotes cancer cell migration and invasion by activating cytoskeletal rearrangements and epithelial-mesenchymal transition.

pANXA2 is an inducible hallmark of diverse solid tumor microenvironments in small animal models and primary human cancer tissues, with its expression confined to tumor regions having elevated calcium levels. Cell surface-associated pANXA2 binds and stabilizes the plasminogen receptor S100A10/p11, which associates with tissue plasminogen activator (tPA) and plasminogen to generate plasmin. The enhanced matrix invasion of tumor cells and migration of tumor-promoting macrophages into tumors. ANXA2 is highly activated (phosphorylated) irrespective of the solid tumor type. In human cancers, pANXA2 is expressed in subtypes of breast cancers, including Er+ and triple-negative cancers, but not in the healthy breast tissue from the same cancer patients. Most ANXA2-based drug delivery strategies rely on the overexpression of ANXA2 in certain tumors. Still, non-tumor tissues also express sufficiently elevated levels to impair selectivity, leading to pre-imaging and tissue biopsy to determine the drugs' usefulness for treating specific tumors.

A variety of cancers are imaged by administering targeted near-infrared (NIR) fluorescence imaging probes. LS301 and LS838 are excellent NIR cancer imaging probes, especially, as disclosed herein, for their specificity toward pANXA2. The clinical formulation for a hydrophobic optical probe should meet several conditions, including adequate and accurate dosing, bioavailability, targeting efficacy, and appropriate absorption and fluorescence characteristics. The long circulation time of LS301 and LS838 delays the tumor uptake and clearance from non-tumor tissue. The formulations described herein accelerate tumor uptake, allowing for quick clinical intervention within an hour post-administration.

SUMMARY

The present disclosure provides stable, sustainable formulations of LS301 and LS838 NIR imaging probes for various biological applications, including lyophilized product, IV injection, topical application, and oral gavage delivery, and doxorubicin conjugates of LS301 and LS838 for targeted cancer treatment.

The present disclosure provides a pharmaceutical composition comprising an effective amount of cypate-Cyclo (Cys-Gly-Arg-Asp-Ser-Pro-Cys)-Lys-OH (LS301), cypate-Cyclo (Cys-Gly-Arg-Asp-Ser-Pro-Cys)-Tyr-OH (LS838), or pharmaceutically acceptable salts thereof, wherein each amino acid residue is independently in a D or L configuration; a divalent metal ion; and a pharmaceutically acceptable carrier.

The present disclosure provides a lyophilized product comprising a dye-conjugate chosen from cypate-Cyclo(Cys-Gly-Arg-Asp-Ser-Pro-Cys)-Lys-OH (LS301), cypate-Cyclo (Cys-Gly-Arg-Asp-Ser-Pro-Cys)-Tyr-OH (LS838) or pharmaceutically acceptable salts thereof, wherein each amino acid residue is independently in a D or L configuration, and albumin, wherein the dye-conjugate and the albumin are in a 1:50 (w/w) ratio.

The present disclosure also provides aa vial comprising about 102 mg of the lyophilized product disclosed herein.

The present disclosure further provides an injectable solution comprising about 102 mg of the lyophilized product disclosed herein and about 10 mL of phosphate-buffered saline.

The present disclosure further provides a method for identifying compromised fibroblasts, comprising administering an effective amount of any pharmaceutical composition disclosed herein to a subject in need thereof.

The present disclosure also provides a method of binding phosphorylated annexin A2 (pANXA2) protein in a biological sample comprising contacting the biological sample with any pharmaceutical composition disclosed herein.

The present disclosure provides doxorubicin-cypate-cyclic(Cys-Gly-Arg-Asp-Ser-Pro-Cys)-Lys-OH) and salts thereof, and pharmaceutical compositions thereof. In certain embodiments, cancer is treated in a subject in need thereof, comprising administering an effective amount of doxorubicin-cypate-cyclic(Cys-Gly-Arg-Asp-Ser-Pro-Cys)-Lys-OH) and/or salts thereof or a pharmaceutical composition of any one doxorubicin-cypate-cyclic(Cys-Gly-Arg-Asp-Ser-Pro-Cys)-Lys-OH) and/or salts thereof to the subject.

DETAILED DESCRIPTION

In one aspect of this disclosure, the accumulation rate, tissue uptake selectivity, and amount of product retained in target tissue are improved. The disclosure is based on the findings that formulating some drugs and imaging agents in uptake excipients or the presence of ionic solutions, such as an electrolyte, can improve the cellular internalization and biodistribution of these products. A general embodiment of this disclosure relates to the formulation of dyes, dye-like molecules, and cyclic or aromatic drugs with excipients such as albumin, polyethylene glycol (PEG), cyclodextrin, and surfactants. The enabling ionic species include cations and anions. Cations include monovalent and multivalent cations such as Na, K, Ba, Ca, Mg, Al, Cu, Fe, and Zr. Anions can be monovalent or multivalent, including chlorides, carbonates, nitrates, cyanines, and sulfonates. An embodiment includes the formulation of LS301 in calcium or magnesium. Another embodiment is the formulation of LS301 in albumin or PEG or dimethylsulfoxide.

LS301 is a cyclic octapeptide labeled with a near-infrared dye which exhibits selective and high-affinity calcium-dependent binding to phosphorylated annexin A2 (pANXA2) protein in diverse solid tumors. LS301 preferentially binds to the invasive edges of tumors, a process amplified by cancer cell-induced pANXA2 expression in tumor-associated stromal cells. Further, it traffics within macrophages to the necrotic core of tumors. High levels of pANXA2 and calcium are present in most solid cancers' microenvironment, revealing a pathway to image and selectively deliver drugs to tumors.

In certain embodiments, the divalent metal ion is chosen from $Ca^{2+}$, $Mg^{2+}$, and $Mn^{2+}$, for example, $Ca^{2+}$. In certain embodiments, the divalent metal ion is present at a concentration between 1 mM and 10 mM, such as 1 mM, 2 mM, 3 mM, 4 mM, 5 mM, 6 mM, 7 mM, 8 mM, 9 mM, or 10 mM. In certain embodiments, the divalent metal ion is present at a concentration of 5 mM.

In certain embodiments, the cypate is

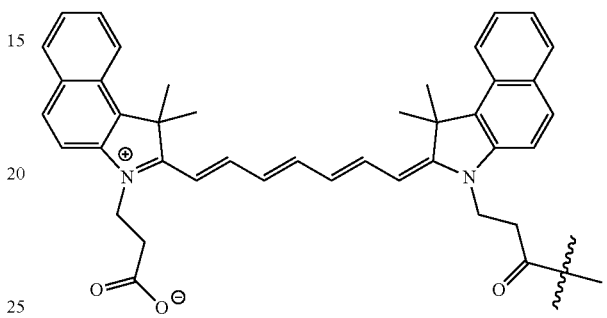

In certain embodiments, at least one of the Cys amino acid residues is D-Cys.

In certain embodiments, the compound is LS301 and comprises the structural formula

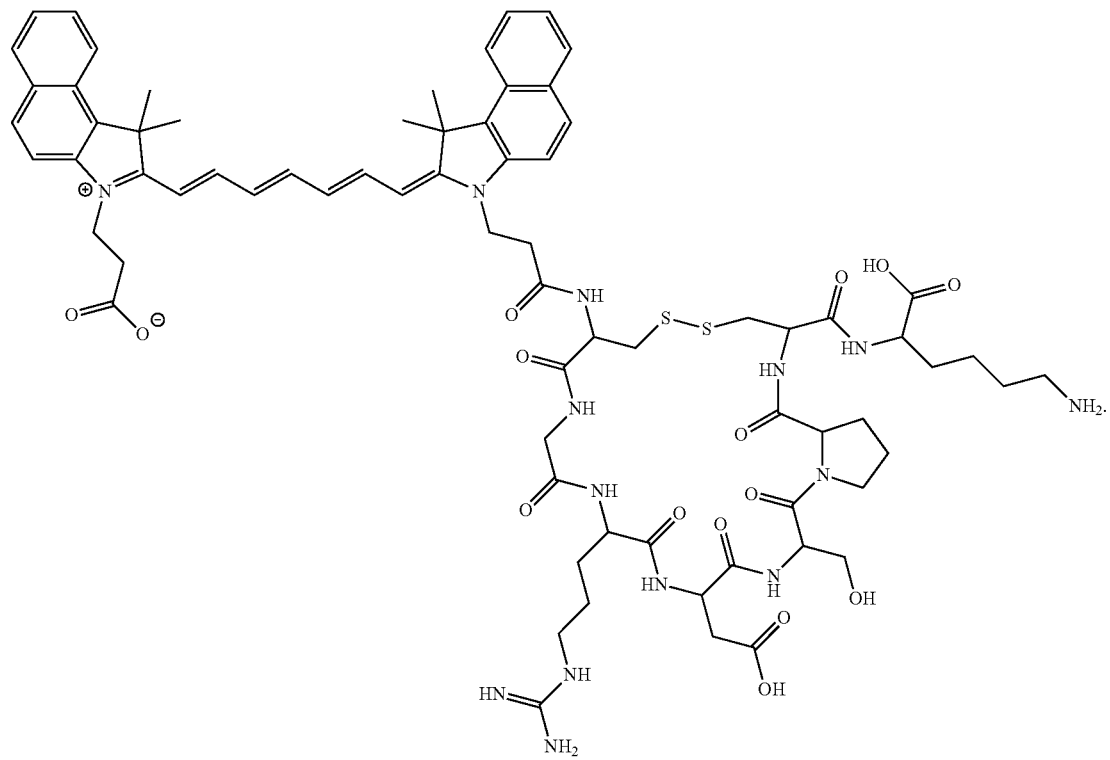 [SMILES: CC1(C)C(/C=C/C=C/C=C/C=C2/N(CCC(=O)NC3CSSCC(C(=O)NC(CCCCN)C(=O)O)NC(=O)C4CCCN4C(=O)C(CO)NC(=O)C(CC(=O)O)NC(=O)C(CCCNC(=N)N)NC(=O)CNC3=O)c3ccc4ccccc4c3C2(C)C)=[N+](CCC(=O)[O-])c2ccc3ccccc3c21]

In certain embodiments, the compound is LS301 comprising the structural formula

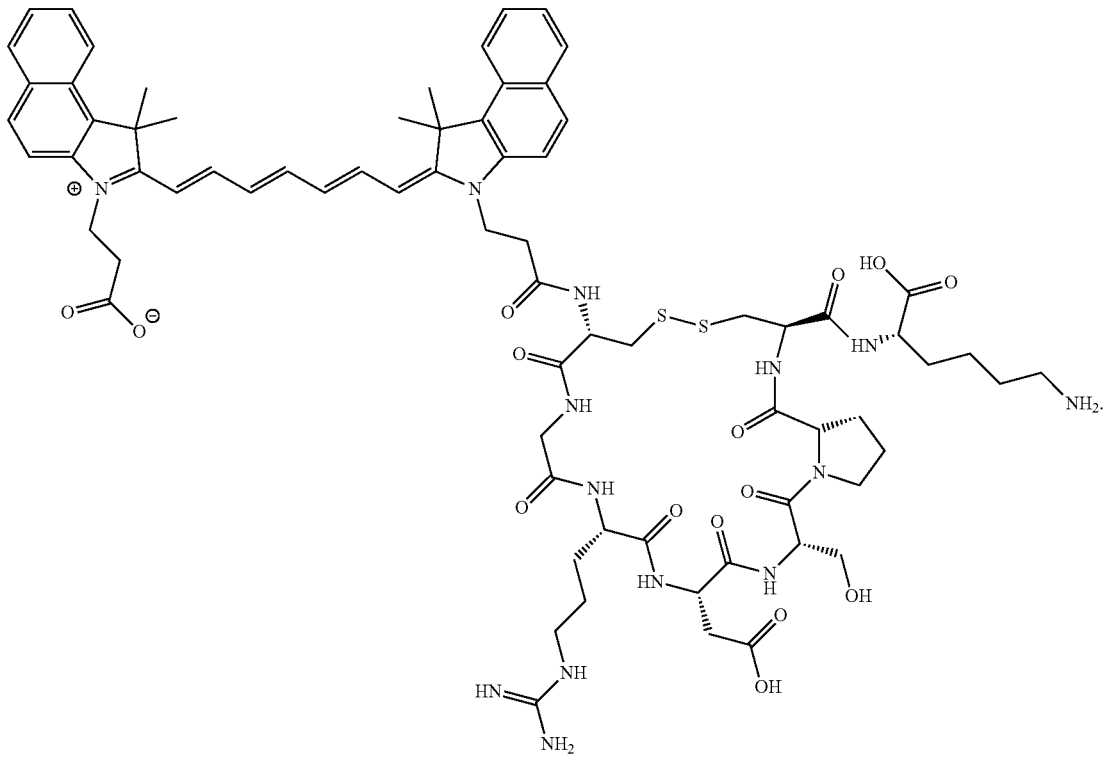

LS301 selectively binds to pANXA2 over the non-activated ANXA2. Histopathology of tissue samples from mice administered with LS301 in vivo showed that the compound accumulates in pANXA2-positive cancer cells. Cancer cells induce pANXA2 expression in tumor-associated fibroblasts and macrophages to stimulate LS301 accumulation in these cells at the periphery and core. By detecting pANXA2-associated cells in the tumor microenvironment, LS301 targets and delivers drugs to multiple types of solid tumors. The preferential localization of LS301 at the proliferating edge and the inner core of solid tumors defines tumor margins, improves cancer resection accuracy during surgery, and treats cancer simultaneously from the periphery and interior core of the tumor.

Uptake of LS301 into the solid cancer cell lines for lung (A549), breast (MDA-MB-231 and 4T1), and myeloid leukemia (HL60) reached a maximum concentration at 12 hours, which maintained over 24 hours. Cypate alone exhibited only transient retention in these cell lines. Without wishing to be bound by theory, initially, LS301 binds to lipid rafts in the cellular plasma membrane, which endocytosed via a clathrin-dependent pathway after one hour of incubation. LS301 was then trafficked into endosomes. After 5 hours, LS301 was primarily found in lysosomes, mitochondria, and peroxisomes.

In certain embodiments, the pharmaceutical composition comprises albumin. The cypate dye moiety of LS301 reversibly binds to the hydrophobic pockets of albumin. Without wishing to be bound by theory, this albumin binding is likely not the primary cause of LS301 tumor uptake. Tumors did not retain cypate in vivo with or without formulation with albumin. Rather, the albumin is a nitrogen source for growing tumors. In certain embodiments, the albumin is chosen from human serum albumin, mouse serum albumin, and bovine serum albumin. In certain embodiments, the albumin is human serum albumin (HSA). In certain embodiments, the albumin is mouse serum albumin (MSA). In certain embodiments, the albumin is bovine serum albumin (BSA).

LS301 preferentially targets ANXA2 over ANXA1 and ANXA3. ANXA2 calcium-dependently associates with cholesterol-rich lipid rafts at cell surfaces. LS301 also localizes to these lipids rafts and binds calcium with an apparent dissociation constant ($K_d$) of 5.67±2.40 nM as determined by microscale thermophoresis (MST). The apparent $K_d$ for LS301 binding to pANXA2, ANXA2, and ANXA3 proteins was 0.075±0.002 nM; 0.389±0.015 nM; and 6.128±0.280 nM, respectively via MST. LS301 preferentially bound to lysates of insulin-stimulated, pANXA2-expressing 4T1 cells with an apparent $K_d$ of 0.017±0.004 nM.

NIR fluorescence microscopy showed that LS301 substantially colocalized with pANXA2 in LS301-treated A549 and 4T1 cells after 1-hour incubation. Cells expressing the wild-type ANXA2 had increased pANXA2 expression and cellular uptake of LS301 upon stimulation with insulin, while cells expressing mutant ANXA2 (Y23A) showed minimal LS301 uptake or pANXA2 expression with insulin stimulation. Tissue plasminogen activator (tPA) protein binds to a site in the N-terminal domain of ANXA2 comprising the amino acid sequence LCKLSL. A synthetic LCKLSL peptide inhibited the binding and internalization of LS301 in cells.

Adding LS301 to fibroblast co-cultured with ANXA2-positive GFP-expressing 4T1 cells resulted in LS301 uptake by tumor cells and fibroblasts. By increasing the population of pANXA2-positive cells for tumor tissue, cancer cells amplify LS301 accumulation. Taken together, these results demonstrate that LS301 is selective for pANXA2, regardless of the cell or cancer type.

LS301 selectively accumulated in a tumor from a breast cancer patient-derived xenograft and remained in the lesion for over 96 hours. Control experiments with cypate alone or with a scrambled LS301 peptide analog (Cypate-cyclo(Cys-Arg-Gly-Asp-Ser-Pro-Cys)-Lys-OH) were not retained. In small tumors (<5 mm), LS301 coverage is about 100%. In advanced tumors, LS301 accumulated at the periphery as correlated to pANXA2 and calcium expression. In capsular tumors such as breast cancer, LS301 intensely fluoresced in tumor cells and cancer-associated fibroblasts. Identifying these compromised fibroblasts enables one to detect dormant cancer cells early and to help prevent subsequent relapse.

In certain embodiments, the pharmaceutical composition comprises the compound LS838. In certain embodiments, LS838 comprises the structural formula

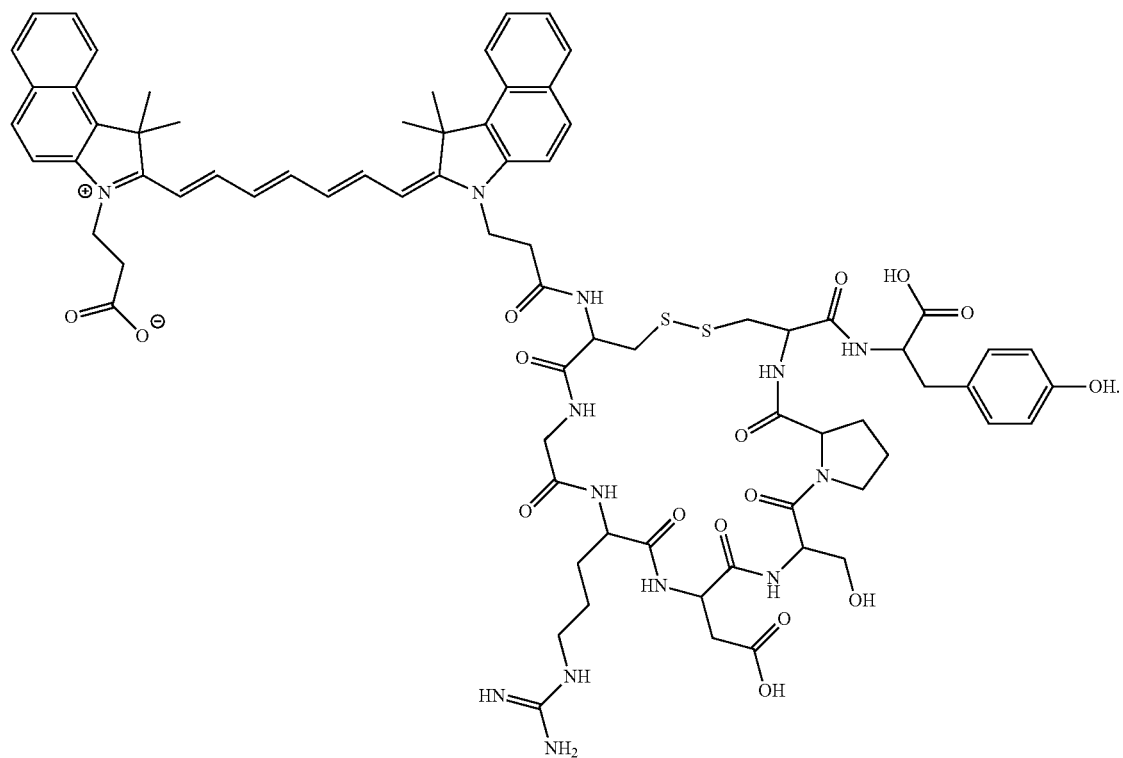 [SMILES: CC1(C)C(/C=C/C=C/C=C/C=C2/N(CCC(=O)NC3CSSCC(C(=O)NC(Cc4ccc(O)cc4)C(=O)O)NC(=O)C4CCCN4C(=O)C(CO)NC(=O)C(CC(=O)O)NC(=O)C(CCCNC(=N)N)NC(=O)CNC3=O)c3ccc4ccccc4c3C2(C)C)=[N+](CCC(=O)[O-])c2ccc3ccccc3c21]

In certain embodiments, the compound is LS838 and comprises the structural formula

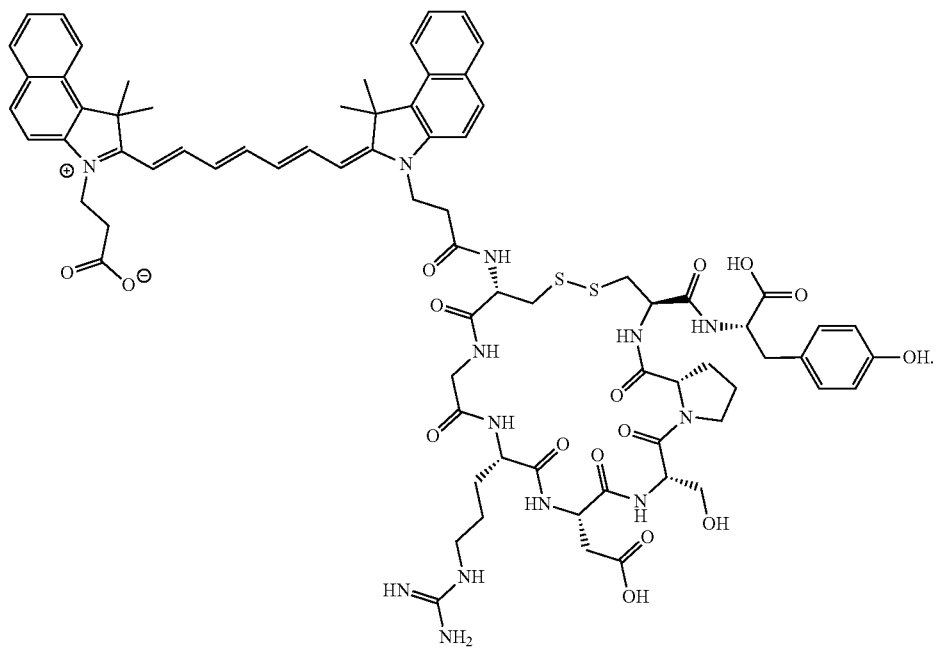 [SMILES: CC1(C)C(/C=C/C=C/C=C/C=C2/N(CCC(=O)N[C@@H]3CSSC[C@@H](C(=O)N[C@@H](Cc4ccc(O)cc4)C(=O)O)NC(=O)[C@@H]4CCCN4C(=O)[C@H](CO)NC(=O)[C@H](CC(=O)O)NC(=O)[C@H](CCCNC(=N)N)NC(=O)CNC3=O)c3ccc4ccccc4c3C2(C)C)=[N+](CCC(=O)[O-])c2ccc3ccccc3c21]

LS838 detects cancerous lesions, such as pancreatic ductal adenosarcoma (PDAC) and pancreatic intraepithelial neoplasia (Pan1N) 2/3 lesions, with high accuracy. Uptake is mediated by the energy needs of these metabolically active cells. LS838 is then trapped intracellularly under the highly reducing environment of these cells. In certain embodiments, applying LS838 to distinguish PDAC and to transform Pan1N from chronic pancreatitis with high accuracy significantly progresses treatment for these cancers.

LS838 enables NIR fluorescence to detect microscopic lesions not visible with prior clinical imaging techniques. LS838 fluoresces more brightly than LS301, allowing smaller amounts of LS838 to achieve the same uptake kinetics as LS301.

Without wishing to be bound by theory, the placement of the tyrosine in the LS838 molecule is important for retaining LS838 in tumors. Unlike LS301, LS838 can be radiolabeled at its tyrosine residue, enabling combined intravital fluorescence microscopy and noninvasive imaging. In certain embodiments, the radionuclide is chosen from, for example, fluorine-18, iodine-123, iodine-124, iodine-125, and iodine-131. This radiolabeling allows the imaging of cancer in the human body noninvasively using nuclear imaging methods. The fluorescence allows optical methods to guide tissue biopsy, surgery, and assessment of surgical margins.

Conjugation of chemotherapeutics, such as doxorubicin, to the free carboxylic acid group of LS838, allows for the highly selective treatment of cancer, including PDAC, with minimal off-target effect on the healthy cells. LS838 selectively remains in diverse tumors without significant loss of fluorescence over time. The high specificity of LS838 for cancer cells in the presence of healthy white blood cells allows the same agent to detect circulating tumor cells (CTCs) without additional tagging or expensive antibodies.

In certain embodiments, the pharmaceutically acceptable carrier comprises phosphate-buffered saline. In certain embodiments, the pharmaceutical composition is administered intravenously. In certain embodiments, the pharmaceutical composition is administered topically, for example, to the subject's colon. In certain embodiments, the pharmaceutical composition is administered orally. In certain embodiments, the effective amount is up to about 0.6 µmol/kg including 0.1 µmol/kg, 0.2 µmol/kg, 0.3 µmol/kg, 0.4 µmol/kg, 0.5 µmol/kg or 0.6 µmol/kg.

The present disclosure further provides a method for identifying compromised fibroblasts, comprising administering an effective amount of the pharmaceutical composition described herein to a subject in need thereof. In certain embodiments, the compromised fibroblasts are proximal to dormant cancer cells.

In certain embodiments, the cancer is chosen from acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

In some embodiments, the cancer is acute lymphoblastic leukemia. In some embodiments, the cancer is acute myeloid leukemia. In some embodiments, the cancer is adrenocortical carcinoma. In some embodiments, the cancer is AIDS-related cancer, such as AIDS-related lymphoma. In some embodiments, the cancer is anal cancer. In some embodiments, the cancer is appendix cancer. In some embodiments, the cancer is astrocytomas (childhood cerebellar or cerebral). In some embodiments, the cancer is basal cell carcinoma. In some embodiments, the cancer is bile duct cancer. In some embodiments, the cancer is bladder cancer. In some embodiments, the cancer is bone cancer. In some embodiments, the cancer is brainstem glioma. In some embodiments, the cancer is brain tumors, such as cerebellar astrocytoma. In some embodiments, the cancer is cerebral astrocytoma/malignant glioma. In some embodiments, the cancer is ependymoma. In some embodiments, the cancer is medulloblastoma. In some embodiments, the cancer is supratentorial primitive neuroectodermal tumors. In some embodiments, the cancer is a visual pathway and hypothalamic gliomas. In some embodiments, the cancer is breast cancer. In some embodiments, the cancer is bronchial adenomas/carcinoids. In some embodiments, the cancer is Burkitt lymphoma. In some embodiments, the cancer is carcinoid tumors (childhood, gastrointestinal). In some embodiments, the cancer is carcinoma of an unknown primary. In some embodiments, the cancer is central nervous system lymphoma (primary). In some embodiments, the cancer is cerebellar astrocytoma. In some embodiments, the cancer is cerebral astrocytoma/malignant glioma. In some embodiments, the cancer is cervical cancer. In some embodiments, the cancer is childhood cancer. In some embodiments, the cancer is chronic lymphocytic leukemia. In some embodiments, the cancer is chronic myelogenous leukemia. In some embodiments, the cancer is a chronic myeloproliferative disorder. In some embodiments, the cancer is colon cancer. In some embodiments, the cancer is cutaneous T-cell lymphoma. In some embodiments, the cancer is a desmoplastic small round cell tumor. In some embodiments, the cancer is endometrial cancer. In some embodiments, the cancer is ependymoma. In some embodiments, the cancer is esophageal cancer. In some embodiments, the cancer is Ewing's sarcoma in the Ewing family of tumors. In some embodiments, the cancer is an extracranial germ cell tumor (childhood). In some embodiments, the cancer is an extragonadal germ cell tumor. In some embodiments, the cancer is extrahepatic bile duct cancer. In some embodiments, the cancer is eye cancer, such as intraocular melanoma retinoblastoma. In some embodiments, the cancer is gallbladder cancer. In some embodiments, the cancer is gastric (stomach) cancer. In some embodiments, the cancer is a gastrointestinal carcinoid tumor. In some embodiments, the cancer is a gastrointestinal stromal tumor. In some embodiments, the cancer is germ cell tumors (childhood extracranial, extragonadal, ovarian). In some embodiments, the cancer is a gestational trophoblastic tumor. In some embodiments, the cancer is gliomas (adult, childhood brain stem. childhood cerebral astrocytoma, childhood visual pathway, and hypothalamic). In some embodiments, the cancer is gastric carcinoid. In some embodiments, the cancer is hairy cell leukemia. In some embodiments, the cancer is head and neck cancer. In some embodiments, the cancer is hepatocellular (liver) cancer. In some embodiments, the cancer is Hodgkin lymphoma. In some embodiments, the cancer is hypopharyngeal cancer. In some embodiments, the cancer is hypothalamic and visual pathway glioma (childhood). In some embodiments, the cancer is intraocular melanoma. In some embodiments, the cancer is islet cell carcinoma. In some embodiments, the cancer is Kaposi sarcoma. In some embodiments, the cancer is kidney cancer (renal cell cancer). In some embodiments, the cancer is laryngeal cancer. In some embodiments, the cancer is leukemia, such as acute lymphoblastic, acute myeloid, chronic lymphocytic, chronic myelogenous, or hairy cell. In some embodiments, the cancer is a lip and oral cavity cancer. In some embodiments, the cancer is liver cancer (primary). In some embodiments, the cancer is lung cancers, such as non-small cell lung cancer and small cell lung cancer. In some embodiments, the cancer is lymphoma, such as AIDS-related, Burkitt, cutaneous T-cell, Hodgkin, non-Hodgkin, and primary central nervous system. In some embodiments, the cancer is macroglobulinemia (Waldenström). In some embodiments, the cancer is malignant fibrous histiocytoma of bone/osteosarcoma. In some embodiments, the cancer is medulloblastoma (childhood). In some embodiments, the cancer is melanoma. In some embodiments, the cancer is intraocular melanoma. In some embodiments, the cancer is Merkel cell carcinoma. In some embodiments, the cancer is mesotheliomas, such as adult malignant and childhood. In some embodiments, the cancer is metastatic squamous neck cancer with occult primary. In some embodiments, the cancer is mouth cancer. In some embodiments, the cancer is multiple endocrine neoplasia syndrome (childhood). In some embodiments, the cancer is multiple myeloma/plasma cell neoplasm. In some embodiments, the cancer is mycosis fungoides. In some embodiments, the cancer is myelodysplastic syndromes. In some embodiments, the cancer is a myelodysplastic/myeloproliferative disease. In some embodiments, the cancer is myelogenous leukemia (chronic). In some embodiments, the cancer is myeloid leukemias, such as adult acute and childhood acute. In some embodiments, the cancer is multiple myeloma. In some embodiments, the cancer is myeloproliferative disorders (chronic). In some embodiments, the cancer is a nasal cavity and paranasal sinus cancer. In some embodiments, the cancer is nasopharyngeal carcinoma. In some embodiments, the cancer is neuroblastoma. In some embodiments, the cancer is non-Hodgkin lymphoma. In some embodiments, the cancer is non-small cell lung cancer. In some embodiments, the cancer is oral cancer. In some embodiments, the cancer is oropharyngeal cancer. In some embodiments, the cancer is osteosarcoma/malignant fibrous histiocytoma of bone. In some embodiments, the cancer is ovarian cancer. In some embodiments, the cancer is ovarian epithelial cancer, such as a surface epithelial-stromal tumor. In some embodiments, the cancer is an ovarian germ cell tumor. In some embodiments, the cancer is an ovarian low malignant potential tumor. In some embodiments, the cancer is pancreatic cancer. In some embodiments, the cancer is pancreatic cancer (islet cell). In some embodiments, the cancer is paranasal sinus and nasal cavity cancer. In some embodiments, the cancer is parathyroid cancer. In some embodiments, the cancer is penile cancer. In some embodiments, the cancer is pharyngeal cancer. In some embodiments, the cancer is pheochromocytoma. In some embodiments, the cancer is pineal astrocytoma. In some embodiments, the cancer is pineal germinoma. In some embodiments, the cancer is pineoblastoma and supratentorial primitive neuroectodermal tumors (childhood). In some embodiments, the cancer is a pituitary adenoma. In some embodiments, the cancer is plasma cell neoplasia. In some embodiments, the cancer is pleuropulmonary blastoma. In some embodiments, the cancer is a primary central nervous system lymphoma. In some embodiments, the cancer is prostate cancer. In some embodiments, the cancer is rectal cancer. In some embodiments, the cancer is renal cell carcinoma (kidney cancer). In some embodiments, the cancer is renal pelvis and ureter transitional cell cancer. In some embodiments, the cancer is retinoblastoma. In some embodiments, the cancer is rhabdomyosarcoma (childhood). In some embodiments, the cancer is salivary gland cancer. In some embodiments, the cancer is sarcoma, such as the Ewing family of tumors, Kaposi, soft tissue, and uterine. In some embodiments, the cancer is Sézary syndrome. In some embodiments, the cancer is skin cancers, such as nonmelanoma and melanoma. In some embodiments, the cancer is skin carcinoma (Merkel cell). In some embodiments, the cancer is small cell lung cancer. In some embodiments, the cancer is small intestine cancer. In some embodiments, the cancer is soft tissue sarcoma. In some embodiments, the cancer is squamous cell carcinoma. In some embodiments, the cancer is squamous neck cancer with occult primary (metastatic). In some embodiments, the cancer is stomach cancer. In some embodiments, the cancer is a supratentorial primitive neuroectodermal tumor (childhood). In some embodiments, the cancer is T-Cell lymphoma (cutaneous). In some embodiments, the cancer is testicular cancer. In some embodiments, the cancer is throat cancer. In some embodiments, the cancer is thymoma (childhood). In some embodiments, the cancer is thymoma and thymic carcinoma. In some embodiments, the cancer is thyroid cancer. In some embodiments, the cancer is thyroid cancer (childhood). In some embodiments, the cancer is transitional cell cancer of the renal pelvis and ureter. In some embodiments, the cancer is a trophoblastic tumor (gestational). In some embodiments, the cancer is an unknown primary site, such as adult and childhood. In some embodiments, the cancer is ureter and renal pelvis transitional cell cancer. In some embodiments, the cancer is urethral cancer. In some embodiments, the cancer is uterine cancer (endometrial). In some embodiments, the cancer is uterine sarcoma. In some embodiments, the cancer is vaginal cancer. In some embodiments, the cancer is a visual pathway and hypothalamic glioma (childhood). In some embodiments, the cancer is vulvar cancer. In some embodiments, the cancer is Waldenström macroglobulinemia. In some embodiments, the cancer is Wilms tumor (childhood).

In certain embodiments, the pharmaceutical composition is administered intravenously. In certain embodiments, the pharmaceutical composition is administered topically, for example, to the subject's colon. In certain embodiments, the pharmaceutical composition is administered orally. In certain embodiments, the pharmaceutical composition is administered anally.

The present disclosure provides a method of binding phosphorylated annexin A2 (pANXA2) protein in a biological sample comprising contacting the biological sample with a pharmaceutical composition disclosed herein. In certain embodiments, the binding is selective over annexin A1 (ANXA1), non-activated ANXA2, and annexin A3 (ANXA3). In certain embodiments, tumor margins of cancer are defined. In certain embodiments, the accuracy of cancer resection is improved during surgery. In certain embodiments, cancer is treated simultaneously from the periphery and interior core of a tumor.

The present disclosure also provides doxorubicin-cypate-cyclic(Cys-Gly-Arg-Asp-Ser-Pro-Cys)-Lys-OH) and salts thereof. In certain embodiments, the cypate is

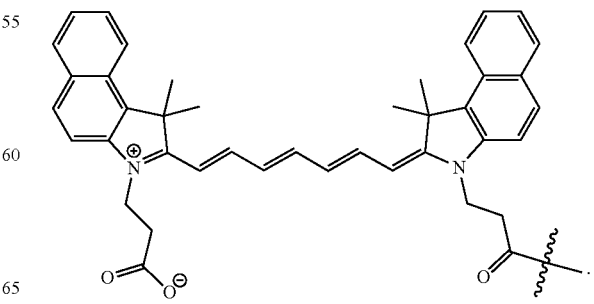

In certain embodiments, at least one of the Cys amino acid residues is D-Cys.

In certain embodiments, the compound has the structural formula

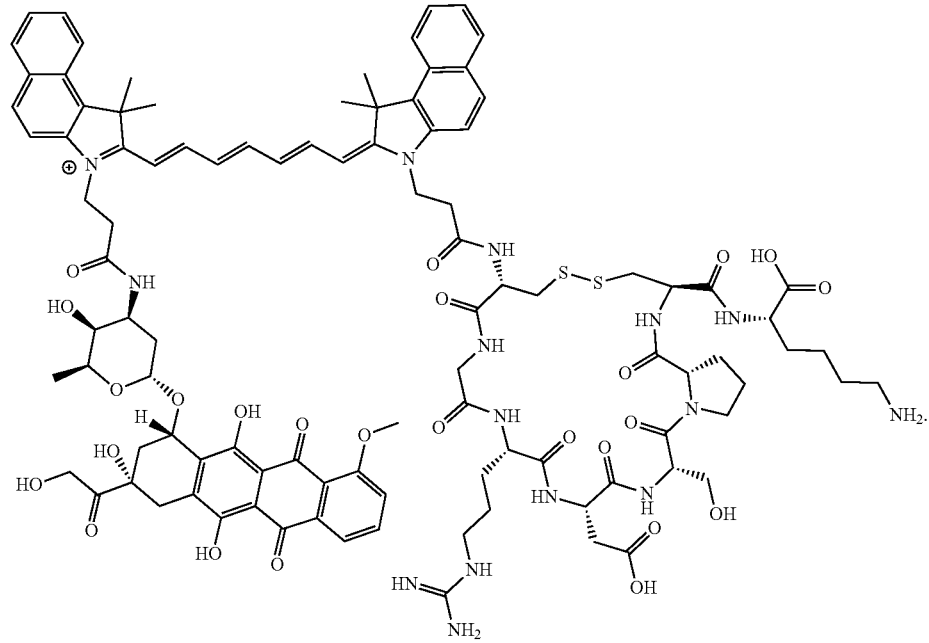 [SMILES: COc1cccc2c1C(=O)c1c(O)c3c(c(O)c1C2=O)C[C@@](O)(C(=O)CO)C[C@@H]3O[C@H]1C[C@H](NC(=O)CC[N+]2=C(/C=C/C=C/C=C/C=C3/N(CCC(=O)N[C@@H]4CSSC[C@@H](C(=O)N[C@@H](CCCCN)C(=O)O)NC(=O)[C@@H]5CCCN5C(=O)[C@H](CO)NC(=O)[C@H](CC(=O)O)NC(=O)[C@H](CCCNC(=N)N)NC(=O)CNC4=O)c4ccc5ccccc5c4C3(C)C)C(C)(C)c3c2ccc2ccccc32)[C@H](O)[C@H](C)O1]

The present disclosure further provides a pharmaceutical composition comprising an effective amount of doxorubicin-cypate-cyclic(Cys-Gly-Arg-Asp-Ser-Pro-Cys)-Lys-OH) or a pharmaceutically acceptable salt thereof and a pharmaceutically acceptable carrier.

In certain embodiments, the pharmaceutical composition further comprises a divalent metal ion, such as one chosen from $Ca^{2+}$, $Mg^{2+}$, and $Mn^{2+}$. In certain embodiments, the divalent metal ion is $Ca^{2+}$. In certain embodiments, the divalent metal ion is present at a concentration between 1 mM and 10 mM, such as 5 mM.

In certain embodiments, the pharmaceutical composition further comprises albumin, such as albumin chosen from human serum albumin, mouse serum albumin, and bovine serum albumin. In certain embodiments, the pharmaceutically acceptable carrier comprises phosphate-buffered saline.

In certain embodiments, the pharmaceutical composition is administered intravenously. In certain embodiments, the pharmaceutical composition is administered topically, for example, to the subject's colon. In certain embodiments, the pharmaceutical composition is administered orally. In certain embodiments, the effective amount up to about 0.6 μmol/kg including 0.1 μmol/kg, 0.2 μmol/kg, 0.3 μmol/kg, 0.4 μmol/kg, 0.5 μmol/kg or 0.6 μmol/kg.

The present disclosure provides a method for treating cancer in a subject in need thereof, comprising administering an effective amount of doxorubicin-cypate-cyclic(Cys-Gly-Arg-Asp-Ser-Pro-Cys)-Lys-OH) and salts thereof, or a pharmaceutical composition of doxorubicin-cypate-cyclic (Cys-Gly-Arg-Asp-Ser-Pro-Cys)-Lys-OH) and/or salts thereof to the subject. Unlike free doxorubicin, the conjugate with LS301 does not accumulate in the heart, thus avoiding dose-limiting toxicity. This same effect is expected for the doxorubicin conjugate with LS838.

The present disclosure provides a lyophilized product comprising a dye-conjugate chosen from cypate-Cyclo(Cys-Gly-Arg-Asp-Ser-Pro-Cys)-Lys-OH (LS301), cypate-Cyclo(Cys-Gly-Arg-Asp-Ser-Pro-Cys)-Tyr-OH (LS838), or pharmaceutically acceptable salts thereof, wherein each amino acid residue is independently in a D or L configuration, and albumin. In certain embodiments, the dye-conjugate and the albumin are in a 1:50 (w/w) ratio. In certain embodiments, the albumin is chosen from human serum albumin, mouse serum albumin, and bovine serum albumin.

In certain embodiments, the lyophilized product may be formed by a method comprising suspending the dye-conjugate in 1% albumin solution at a ratio of 1 gram of dye-conjugate per 10 liters of the albumin solution, mixing the suspension, filtering the mixed suspension, and lyophilizing the filtered suspension to form the lyophilized product. In certain embodiments, the suspension is mixed on a shaker of at least about 30 minutes. In certain embodiments, the concentration of the dye-conjugate and albumin in the suspension is measured via absorbance.

The present disclosure further provides a vial comprising about 102 mg of the lyophilized product described herein. In certain embodiments, an injectable solution comprises about 102 mg of the lyophilized product of any one of claims 20 to 24 and about 10 mL of phosphate-buffered saline. In certain embodiments, the injectable solution comprises about 0.2 mg/mL dye-conjugate.

The present disclosure also provides a method of preparing an injectable solution. The method comprises mixing about 10 mL of phosphate-buffered saline into a vial comprising about 102 mg of the lyophilized product described herein to form an injectable solution comprising about 0.2 mg/mL dye-conjugate.

EMBODIMENTS

Provided herein are the following specific embodiments:

Embodiment 1. A pharmaceutical composition comprising an effective amount of cypate-Cyclo(Cys-Gly-Arg-Asp-Ser-Pro-Cys)-Lys-OH (LS301), cypate-Cyclo(Cys-Gly-Arg-Asp-Ser-Pro-Cys)-Tyr-OH (LS838) or pharmaceutically acceptable salts thereof, wherein each amino acid residue is independently in a D or L configuration; a divalent metal ion; and a pharmaceutically acceptable carrier.

Embodiment 2. The pharmaceutical composition of Embodiment 1, wherein the divalent metal ion is chosen from $Ca^{2+}$, $Mg^{2+}$, and $Mn^{2+}$.

Embodiment 3. The pharmaceutical composition of Embodiment 2, wherein the divalent metal ion is $Ca^{2+}$.

Embodiment 4. The pharmaceutical composition of any preceding Embodiment, wherein the divalent metal ion is present at a concentration between 1 mM and 10 mM.

Embodiment 5. The pharmaceutical composition of Embodiment 4, wherein the divalent metal ion is present at a concentration of 5 mM.

Embodiment 6. The pharmaceutical composition of any preceding Embodiment, wherein the cypate is

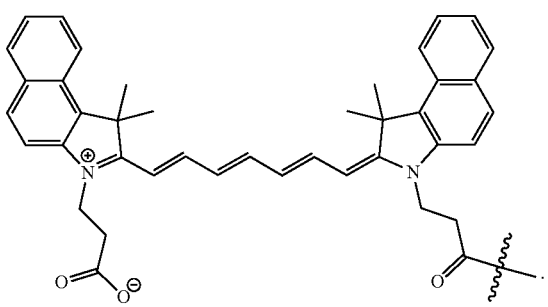 [SMILES: *C(=O)CCN1/C(=C/C=C/C=C/C=C/C2=[N+](CCC(=O)[O-])c3ccc4ccccc4c3C2(C)C)C(C)(C)c2c1ccc1ccccc21]

Embodiment 7. The pharmaceutical composition of any preceding Embodiment, wherein at least one of the Cys amino acid residues is D-Cys.

Embodiment 8. The pharmaceutical composition to Embodiment 1, wherein the compound is LS301 comprising the structural formula

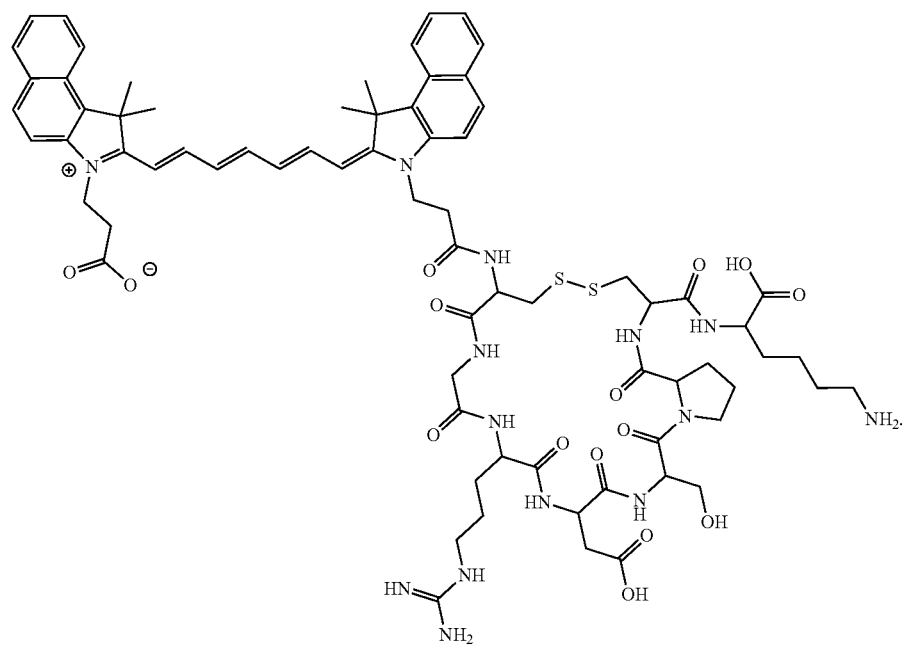 [SMILES: CC1(C)C(/C=C/C=C/C=C/C=C2/N(CCC(=O)NC3CSSCC(C(=O)NC(CCCCN)C(=O)O)NC(=O)C4CCCN4C(=O)C(CO)NC(=O)C(CC(=O)O)NC(=O)C(CCCNC(=N)N)NC(=O)CNC3=O)c3ccc4ccccc4c3C2(C)C)=[N+](CCC(=O)[O-])c2ccc3ccccc3c21]

Embodiment 9. The pharmaceutical composition to Embodiment 8, wherein the compound is LS301 comprising the structural formula
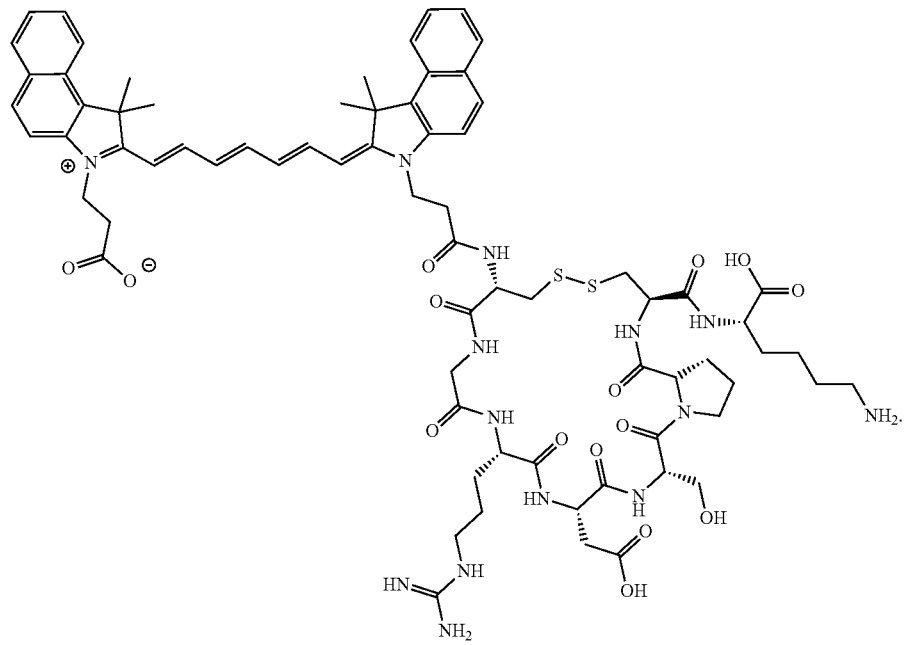
Embodiment 10. The pharmaceutical composition to Embodiment 1, wherein the compound is LS838 comprising the structural formula
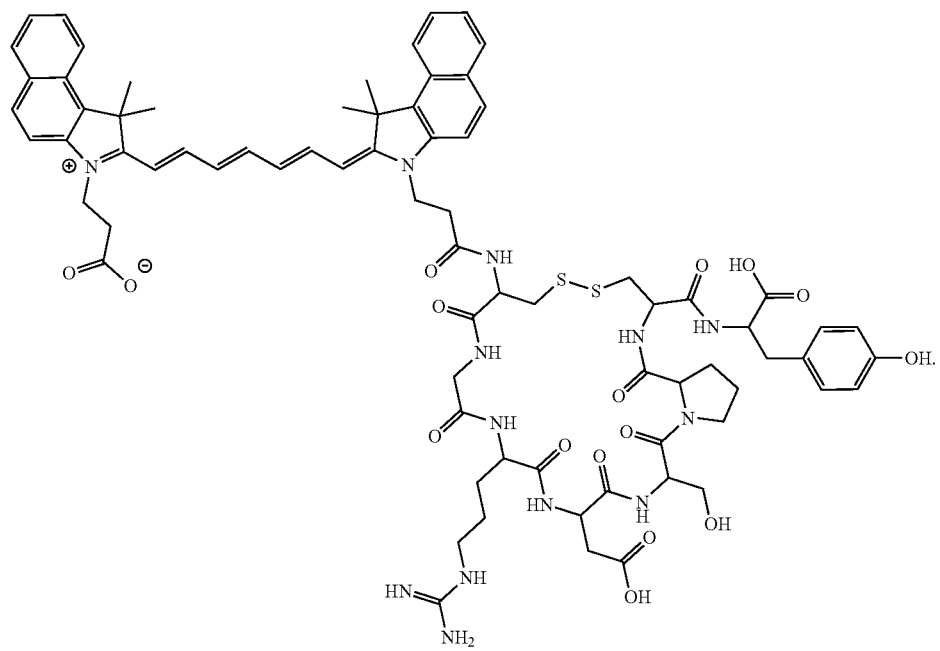 [SMILES: CC1(C)C(/C=C/C=C/C=C/C=C2/N(CCC(=O)NC3CSSCC(C(=O)NC(Cc4ccc(O)cc4)C(=O)O)NC(=O)C4CCCN4C(=O)C(CO)NC(=O)C(CC(=O)O)NC(=O)C(CCCNC(=N)N)NC(=O)CNC3=O)c3ccc4ccccc4c3C2(C)C)=[N+](CCC(=O)[O-])c2ccc3ccccc3c21]

Embodiment 11. The pharmaceutical composition of Embodiment 9, wherein the compound is LS838 comprising the structural formula

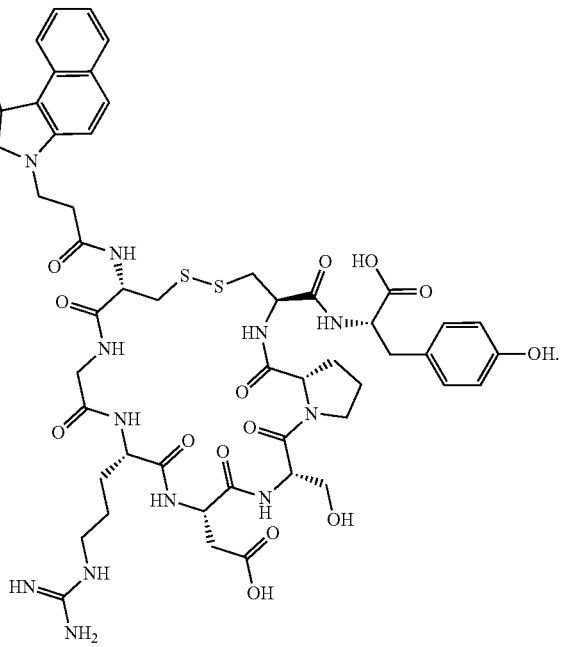

Embodiment 12. The pharmaceutical composition of any preceding Embodiment, further comprising albumin.

Embodiment 13. The pharmaceutical composition of Embodiment 12, wherein the albumin is chosen from human serum albumin, mouse serum albumin, and bovine serum albumin.

Embodiment 14. The pharmaceutical composition of any preceding Embodiment, wherein the pharmaceutically acceptable carrier comprises phosphate-buffered saline.

Embodiment 15. The pharmaceutical composition of any preceding Embodiment formulated for intravenous administration.

Embodiment 16. The pharmaceutical composition of any one of Embodiments 1-14 formulated for topical administration.

Embodiment 17. The pharmaceutical composition of any preceding Embodiment, wherein the effective amount is 0.2 µmol/kg.

Embodiment 18. The pharmaceutical composition of any one of Embodiments 1-16, wherein the effective amount is 0.4 µmol/kg.

Embodiment 19. The pharmaceutical composition of any one of Embodiments 1-16, wherein the effective amount is 0.6 µmol/kg.

Embodiment 20. A method for identifying compromised fibroblasts, comprising administering an effective amount of the pharmaceutical composition of any preceding Embodiment to a subject in need thereof.

Embodiment 21. The method of Embodiment 20, wherein the compromised fibroblasts are proximal to dormant cancer cells.

Embodiment 22. The method of Embodiment 21, wherein the dormant cancer cells are chosen from acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

Embodiment 23. The method of Embodiment 22, wherein the dormant cancer cells are pancreatic cancer.

Embodiment 24. The method of Embodiment 21, wherein the pharmaceutical composition is administered intravenously.

Embodiment 25. The method of Embodiment 21, wherein the pharmaceutical composition is administered topically.

Embodiment 26. The method of Embodiment 21, wherein the topical administration is to the subject's colon.

Embodiment 27. A method of binding phosphorylated annexin A2 (pANXA2) protein in a biological sample comprising contacting the biological sample with a pharmaceutical composition of any one of Embodiments 1-19.

Embodiment 28. The method of Embodiment 27, wherein the binding is selective over annexin A1 (ANXA1), non-activated ANXA2, and annexin A3 (ANXA3).

Embodiment 29. The method of Embodiment 27, wherein tumor margins of cancer are defined.

Embodiment 30. The method of Embodiment 27, wherein the accuracy of cancer resection is improved during surgery.

Embodiment 31. The method of Embodiment 27, wherein cancer is treated simultaneously from the periphery and interior core of a tumor.

Embodiment 32. The method of any one of Embodiments 29-31, wherein the cancer is chosen from acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

EXAMPLES

General Methods

Chemicals. All the fluorenylmethyloxycarbonyl (Fmoc) amino acids, Wang resin Fmoc-Tyr (tBu)-Wang resin, and Fmoc-Lys(Boc)-Wang Resin were purchased from AAPPTec (Louisville, KY, USA). Dichloromethane (DCM), acetic acid, acetic anhydride, thioanisole, phenol, hydroxybenzotriazole (HOBt), N,N-diisopropylethylamine (DIEA), N-trityl-1,2-ethanediamine, phenol, thioanisol, dimethylformamide (DMF), N,N'-diisopropylcarbodiimide (DIC), trifluoroacetic acid (TFA), iodine, methyl tert-butyl ether (MTBE) and O-(7-azabenzotriazol-1-yl)-N,N,N',N'-tetramethyluronium hexafluorophosphate (HATU) were purchased from Sigma-Aldrich (St. Louis, MO, USA). Water was obtained from a Millipore Q3 system. Lysotracker, BODIPY TR Ceramide, CellLight Peroxisome-GFP, BacMam 2.0, and Fluor-4 calcium probe were purchased from Thermo Fisher Scientific (Waltham, MA). Chlorpromazine hydrochloride, filipin complex, and amiloride hydrochloride were purchased from Sigma-Aldrich (St Louis, MO, USA). Reagents for organelle staining included VectaCell Rhodamine 123 (Vector Laboratories, Burlingame, CA, USA).

Recombinant proteins and antibodies. Recombinant annexin A2, annexin A2 with glutathione-S-transferase (GST) tag, annexin A1, and annexin A3 proteins were purchased from MyBioSource, Inc. (San Diego, CA, USA). Purified ANXA2 protein and purified pANXA2 protein were gifts from Dr. Gabriel Bimme (Beth Israel Deaconess Medical Center, Boston, MA). Rabbit monoclonal anti-annexin A2 antibody (D11G2, #8235), Rabbit monoclonal anti-Rab5 (C8B1, #3547), and rabbit monoclonal anti-Rab7 (D95F2, #936 7) primary antibodies were purchased from Cell Signaling Technology, Inc. (Danvers, MA, USA). Mouse monoclonal anti-β-actin 2A3 (sc-517582), mouse monoclonal anti-pANXA2 antibody (11.Tyr 24) (sc-135752), rabbit polyclonal anti-NOS2 (C-19, sc-649), rabbit polyclonal anti-ARG1 (H-52, sc-20150) antibodies, and protein A/G agarose were purchased from Santa Cruz Biotechnology, Inc. (Dallas, TX, USA). Rabbit polyclonal anti-pANXA2 (phosphor-Tyr24) antibody was purchased from Signalway Antibody (College Park, MD, USA). Rabbit polyclonal anti-LS301 antibody was generated by Antibody Research Corporation (St. Charles, MO, USA) via immunization of New Zealand rabbits with keyhole limpet hemocyanin (KLH)-conjugated LS301 followed by antigen affinity purification of rabbit immunoglobulins from blood; antibody titer was tested by ELISA. Tyr24-phosphorylated ANXA2 protein (pANXA2) was generated via in vitro phosphorylation by overnight incubation of recombinant ANXA2 protein with recombinant ephrin B1 (kinase) and ATP in a buffer. The Vybrant Alexa Fluor 488 lipid raft labeling kit was purchased from Thermo Fisher Scientific (Waltham, MA, USA).

Plasmids. Human Anxa2 eDNA subcloned into the pCMV6-AC-GFP vector was purchased from OriGene Technologies (Rockville, MD, USA). cDNA for the mutant pEZ-M98-GFP-Anxa2-Y23A (tyrosine replaced by alanine) was obtained from GeneCopoeia (Rockville, MD, USA). The recombinant plasmids were characterized by restriction digest, and the quality of the expressed recombinant protein was assessed by confocal microscopy for fluorescence integrity and by western blot.

Cell lines and culture. The cancer cell lines 4T1, Lewis Lung Carcinoma (LLC), A431, A549, MDA-MB-231, BxPC-3, and HL-60, were purchased from the American Type Culture Collection (ATCC, Manassas, VA, USA). The 4T1-luciferase (4T1-luc) cell line was a gift from Dr. Katherine Weilbaecher (Washington University School of Medicine, St Louis, MO, USA). Human dermal fibroblasts were obtained from Coriell Cell Technologies (Camden, NJ, USA). Unless otherwise indicated, all cell lines were cultured at 37° C. in a 5% $CO_2$ incubator in appropriate media supplemented with 10% FBS.

Animals. Five to seven-week-old nude Balb/c or C57BL/6 mice were purchased from Charles River Laboratories (Wilmington, MA) and housed in designated animal facilities. Mice were fed ad libitum and inspected regularly. All animal studies were approved by the Washington University School of Medicine Animal Studies Committee (protocol numbers 20130207 and 20160207) and performed per humane care and use of research animals. Human tissues De-identified human breast tissue sections including malignant triple-negative (n=4) and ER-positive (n=4) and control normal tissues (n=3) from the breast cancer patients were obtained from the Tissue Procurement Core (TPC)—Siteman Cancer Center and Pathology and Immunology at Washington University School of Medicine (St, Louis, MO, USA) per Washington University's Institutional Review Board.

Statistics. Unless otherwise noted, differences between sample means were analyzed by a two-tailed unpaired t-test with $p<0.05$ denoting statistical significance. Error bars denote standard error (standard deviation/square root of n); for replicate experiments, the sample size was at least (n)=3 for each experimental group, and data were taken from different samples. Pearson's correlation coefficient, image quantification, and analysis were calculated using the ImageJ software plugin Colocalization Finder. Statistical analyses of the images were performed using Origin Pro 8.0 software (OriginLabs).

Example 1—Synthesis of LS301

LS301 (cypate-cyclic ($_D$Cys-Gly-Arg-Asp-Ser-Pro-Cys)-Lys-OH) was synthesized from the linear GRD peptide, H-$_D$Cys(Acm)-Gly-Arg(Pbf)-Asp(tBu)-Ser(tBu)-Pro-Cys (Acm)-Lys (Boc)-OH, was prepared via a CEM Liberty Blue microwave peptide synthesizer (Matthews, NC, USA) on the Fmoc-Lys(Boc)-Wang resin. The resin (0.1 mmol) was swelled in dichloromethane for 1 hour before use. Fmoc-amino acids (0.5 mmol, 5 eq), coupling reagent (HBTU, 0.5 mmol, 5 eq), and diisopropylethylamine (DIEA, 1 mmol, 10 eq) were added to the resin, and the mixture was reacted for 15 min under microwave irradiation (100 W, 90° C.). The resin was washed three times with DMF. The Fmoc group's deprotection was carried out by treatment of 20% piperidine/DMF for 5 min under microwave irradiation (100 W, 90° C.). The peptidyl resin was washed, and the peptide cyclized through the disulfide bridge with iodine (1.2 eq) in DMF for 90 min.

Subsequently, cypate (3 eq) was conjugated to the cyclic peptide on a solid support in the presence of N,N'-diisopropylcarbodiimide (DIC, 5 eq) in DMF to afford the LS301 peptidyl resin. The resin was then treated with a trifluoroacetic acid cleavage cocktail: thioanisol: phenol: water (85:5:5:5, v/v/v/v) for 90 min at room temperature. The cleaved peptide product was concentrated in vacuo before purifying via reverse-phase HPLC (Gilson, Middleton, WI, USA). The molecular weight of the final product (1469 Da) was confirmed by electrospray ionization mass spectrometry with peaks observed at 1470 (M+1) and 735 (M+2/2).

Example 2—Synthesis of LS301 Peptide (LS637)

LS637 (Ac-Cyclo($_D$Cys-Gly-Arg-Asp-Ser-Pro-Cys)-Lys-OH), a non-fluorescent analog of LS301, was synthesized by a similar method as LS301, except acetic anhydride was used instead of cypate. The molecular weight of the final product (904 Da) was confirmed by electrospray ionization mass spectrometry with peaks observed at 905 (M+1) and 453 (M+2/2).

Example 3—Synthesis of ANXA2 Blocking (LCKLSL) and Scrambled (LGKLSL) Peptides

AnXA2 binding and scrambled peptides, LCKLSL, and LGKLSL, were synthesized on solid support by standard automated Fmoc chemistry at room temperature. Starting with the Rink amide resin (30 μmol), amino acids were subsequently coupled to the resin using the appropriate Fmoc-protected amino acids (90 μmol) and coupling reagent 2-(1H-benzotriazol-1-yl)-1,1,3,3-tetramethyluronium hexafluorophosphate (HBTU, 90 μmol), hydroxybenzotriazole (HOBT, 90 μmol), and N,N-diisopropylethylamine DIEA, 180 μmol). Cleavage of the peptide from the resin and concomitant removal of all protecting groups was achieved with 95% trifluoroacetic acid (TFA) and 5% water. The resulting product was purified by preparative HPLC using a Grace Vydac™ C-18 column (250×21.2 mm) with a UV detector at 254 nm. The desired compound was obtained by linear gradient elution using solvents A (0.1% TFA in water) and B (0.1% TFA in acetonitrile) from 90% to 10% over 30 minutes at 10 mL/min. Analytical HPLC characterized the purity of the peptide. The identity was confirmed by electrospray mass spectrometry (ES+MS): LCKLSL, calculated MW 676 g/mol, observed m/z 677 (M+1); LGKLSL calculated 629.80 g/mol, observed m/z 575 (M+1).

Example 4—Synthesis of KLH-Conjugated LS301 for Antibody Production

Synthesis of KLH-conjugated LS301 was accomplished via conjugation of the linker to LS301 followed by the conjugation of LS301-linker to KLH. For linker conjugation, 180 μmol (34.5 mg) 1-ethyl-3-(3-dimethylaminopropyl)carbodiimide hydrochloride (EDC·HCl, 90 μmol, 41 mg), S-trityl-L-cystine tert-butyl ester hydrochloride (Chem-Impex, Wood Dale, IL, USA), and DIEA (180 μmol, 31.2 μL) in 2 mL DMF was sonicated until clear. The solution was added to 30 μmol LS301 and mixed overnight before the resin was filtered and washed with DMF and DCM. Finally, the product was cleaved from the resin and purified by reverse-phase HPLC. About 3 mg of the product was obtained (MW 1572 g/mol).

Example 5—Synthesis of LS301-Doxorubicin Conjugate (LS766)

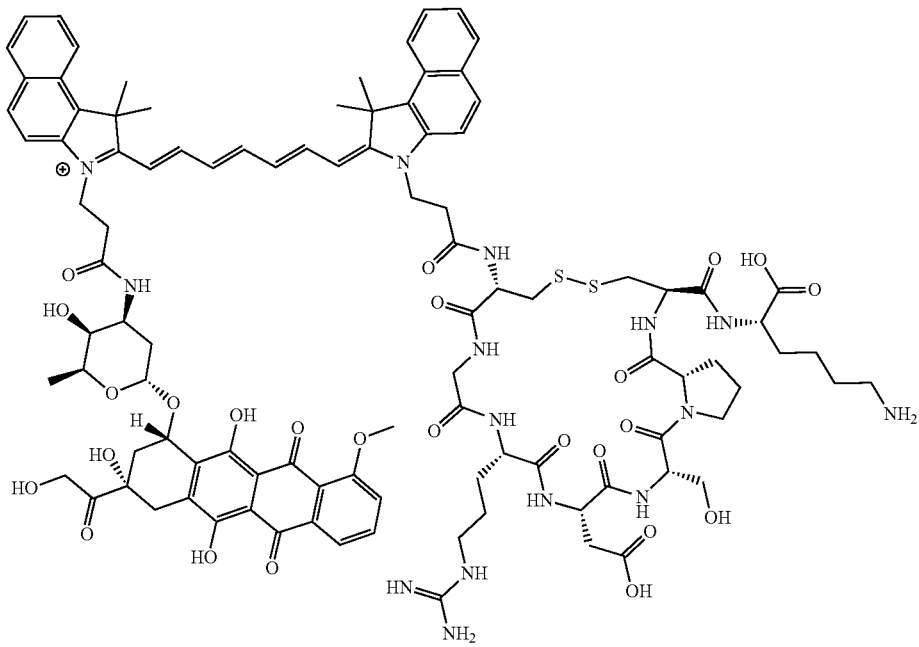 [SMILES: COc1cccc2c1C(=O)c1c(O)c3c(c(O)c1C2=O)C[C@@](O)(C(=O)CO)C[C@@H]3O[C@H]1C[C@H](NC(=O)CC[N+]2=C(/C=C/C=C/C=C/C=C3/N(CCC(=O)N[C@@H]4CSSC[C@@H](C(=O)N[C@@H](CCCCN)C(=O)O)NC(=O)[C@@H]5CCCN5C(=O)[C@H](CO)NC(=O)[C@H](CC(=O)O)NC(=O)[C@H](CCCNC(=N)N)NC(=O)CNC4=O)c4ccc5ccccc5c4C3(C)C)C(C)(C)c3c2ccc2ccccc32)[C@H](O)[C@H](C)O1]

Doxorubicin (3 eq, LC Laboratories, Woburn, MA) was added to a mixture of the LS301 peptidyl resin, (1-[bis(dimethylamino)methylene]-1H-1,2,3-triazolo[4,5-b]pyridinium 3-oxide hexafluorophosphate (HATU, 6 eq), and DIEA (6 eq) in DMF. After 12 hours of reaction, the resin was treated with a cleavage cocktail consisting of TFA: thioanisol: phenol: water (85:5:5:5, v/v/v/v) for 90 minutes at room temperature. The cleaved peptide product was concentrated in Vacuo, then purified on reverse-phase HPLC (Gilson, Middleton, WI, USA) to obtain LS766 (doxorubicin-cypate-cyclic($_D$Cys-Gly-Arg-Asp-Ser-Pro-Cys)-Lys-OH), M/W 1995 g/mol, ESI-MS observed 998 (M+2/2) and 666 (M+3/3).

Following the procedure above, the LS838 peptidyl resin can be reacted with doxorubicin to yield doxorubicin-cypate-cyclic($_D$Cys-Gly-Arg-Asp-Ser-Pro-Cys)-Tyr-OH, comprising the structural formula

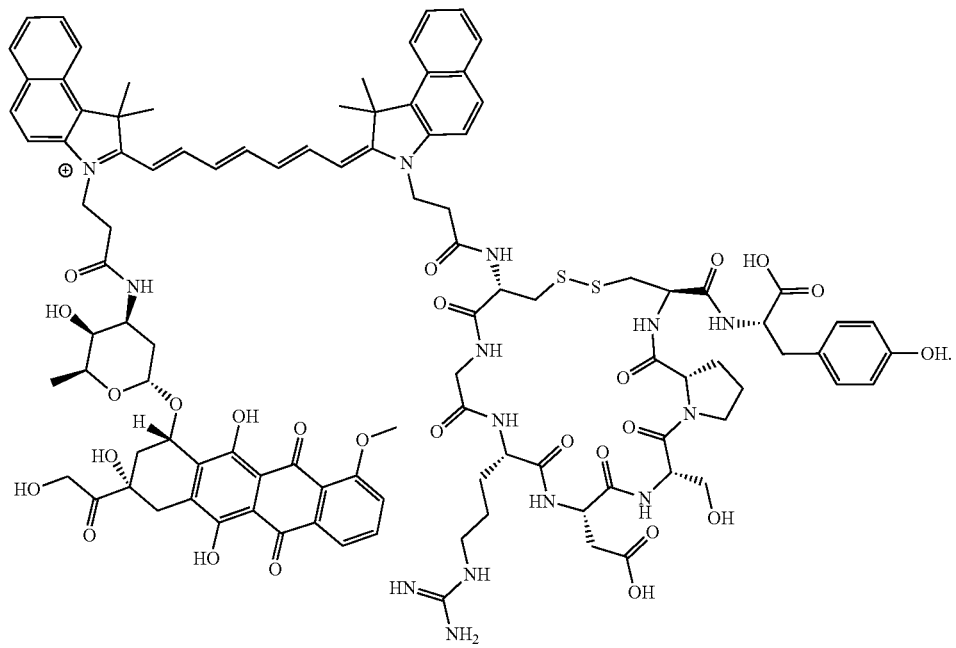 [SMILES: COc1cccc2c1C(=O)c1c(O)c3c(c(O)c1C2=O)C[C@@](O)(C(=O)CO)C[C@@H]3O[C@H]1C[C@H](NC(=O)CC[N+]2=C(/C=C/C=C/C=C/C=C3/N(CCC(=O)N[C@@H]4CSSC[C@@H](C(=O)N[C@@H](Cc5ccc(O)cc5)C(=O)O)NC(=O)[C@@H]5CCCN5C(=O)[C@H](CO)NC(=O)[C@H](CC(=O)O)NC(=O)[C@H](CCCNC(=N)N)NC(=O)CNC4=O)c4ccc5ccccc5c4C3(C)C)C(C)(C)c3c2ccc2ccccc32)[C@H](O)[C@H](C)O1]

with live cells, 4T1 cells in a T-75 flask at about 80% confluence were incubated with LS301 (10 μM) for 24 h at 37° C.; the cells were rinsed with PBS, harvested using trypsin-EDTA, and lysed as above. Next, 10 μg of anti-LS301 polyclonal Ab (Antibody Research Corp., St. Charles, MO) was added to the sample and incubated for 18 hours at 4° C. Forty μL of protein A/G PLUS-agarose beads (Santa Cruz Biotechnology) was then added and incubated overnight at 4° C. under rotation. The pellets were collected by centrifugation (1200×g) and washed three times with 1×PBS for 5 minutes. The pellets were resuspended in 60 μL of 1×electrophoresis loading buffer containing sodium dodecyl sulfate (SDS). Samples were boiled for 7 min. Then 30 μL of the samples were resolved on TGX gels (Any Size gradient TGX gels, Bio-Rad) and visualized by near-infrared fluorescence imaging using the Pearl Imaging System, Coomassie staining, or Western blot analysis.

Example 6—Immunoprecipitation

In general, immunoprecipitation experiments were performed by incubation of LS301 with either 4T1 cell lysates or live 4T1 cells, followed by pulldown of LS301-associated proteins with anti-LS301 antibody and protein A/G agarose beads. For cell lysis, whole 4T1 cells were homogenized in a 15-mL tube on homogenizer using 3 mL of homogenizing RIPA buffer (10 mM Tris-HCl pH 8.0, 140 mM NaCl, 1 mM EDTA, 0.5 mM EGTA, 1% Triton X-100, 0.1% sodium deoxycholate. 0.1% SDS, 1 mM PMSF, protease inhibitor cocktail III (10 μL/mL Calbiochem, 539134), and phosphatase inhibitor cocktail 1 (10 μL/mL, Sigma, P2850)). Lysates were clarified by centrifugation at 15,000× g. The protein concentration was determined by BAC protein assay (Bio-Rad) with bovine serum albumin (BSA) as a standard. The supernatants were stored at −80° C.

For immunoprecipitation studies with cell lysates, 400 μg of cellular protein extract was incubated with LS301 (40 μM) in 0.5 mL 1× phosphate-buffered saline (PBS) for 2 hours at room temperature. For immunoprecipitation studies For fluorescent gel binding experiments, 1 μg recombinant annexin A2 protein was incubated with LS301 or cypate (10 μM) at 37° C. for the periods indicated. Samples were subjected to SDS-PAGE on precast gels (Bio-Rad, Hercules, CA), and gels were imaged for near-infrared fluorescence (800 nm) using a Pearl Small Animal Imager (LI-COR Biosciences, Lincoln, NE, USA). For competitive binding experiments, Annexin A2-GST, annexin A1, or annexin A3 (1.0 μg protein per sample) was pre-incubated with or without 2.5 mM of LS637 (non-fluorescent LS301 analog; blocking peptide) in binding buffer (25 mM Tris-HCl pH 7.4, 150 mM NaCl, 1 mM MgCl$_2$, 1 mM CaCl$_2$) for 1 hour at 37° C. Ten μM. LS301 was then added to each sample. After incubation for 2 hours at 37° C., proteins were subjected to SDS-PAGE and imaged fluorescently. For some experiments, LS301 was incubated with 4T1 tumor cells before SDS-PAGE.

Microscale thermophoresis (MST) studies biomolecular interactions in an aqueous environment without immobilization. MST exploits the directed movement of molecules along a microscopic temperature gradient. The movement rate and direction of movement depend on the species' size, charge, and solvation shell under study. Changes in this environment can change the thermophoretic movement of the species. MST can distinguish very small changes that occur, for example, when a small fluorescent molecule binds to the surface of a protein.

MST was performed using the Monolith NT.115 (Nanotemper Technologies, Munich, Germany). The appropriate agent(s) and LS301 stock samples were denatured in MST-1 buffer (50 mM Tris-HCl, pH 7.4; 150 mM NaCl; 10 mM $MgCl_2$; 2% DMSO; 0.1% Tween-20; 4% SDS, 4 mM dithiothreitol (DTT)) at 97° C. for 10 min. Fluorescence was assessed in MST-2 buffer (50 mM Tris-HCl, pH 7.4; 150 mM NaCl; 10 mM $MgCl_2$). The protein was prepared in MST-2 buffer, and 20 µL serial dilutions were made with protein concentration ranging from 3.05 pM to 50 nM (pANXA2) or 3.81 pM to 62.5 nM (ANXA2). All samples were loaded into NT.115 standard capillaries. The analysis was performed at 37° C., 30% LED power, 60% MST power, and a constant LS301 concentration of 20 nM. The apparent $K_d$ values were calculated from fragment concentration-dependent changes in normalized fluorescence (Fraction Bound) of LS301 after 5 seconds of thermophoresis based on mass action law using the MO Affinity Analysis v2.3 software.

For Western blot analysis, cells were homogenized using an ultrasonic processor in radioimmunoprecipitation assay (RIPA) buffer (10 mM Tris-HCl, pH 8.0; 140 mM NaCl; 1 mM ethylenediaminetetraacetic acid (EDTA); 0.5 mM egtazic acid (EGTA); 1% Triton X-100; 0.1% sodium deoxycholate; 0.1% SDS; 1 mM PMSF). Total cell lysates were clarified by centrifugation. Total cellular protein or pure proteins were denatured in SDS gel-loading buffer (100 mM Tris-HCl, 200 mM DTT, 4% SDS, 0.2% bromophenol blue, and 20% glycerol) for 7 minutes at 100° C. and then separated on 12% TGX gel (Bio-Rad, Hercules, CA, USA). After electrophoresis, proteins were transferred to PVDF-FL membrane using an EC140 Mini Blot Module (Thermo EC, Holbrook, NY, USA) apparatus. The membrane was treated with Odyssey blocking buffer for 1 hour at room temperature, followed by incubation with rabbit monoclonal anti-annexin A2 (D11G2, Cell Signaling Technology, Inc.) and mouse monoclonal pannexin II (11.Tyr24; Santa Cruz Biotechnology) or rabbit ANXA2 (Phospho-Tyr24; MyBioSource, Inc.) primary antibodies in Odyssey blocking buffer at 4° C. overnight. After washing three times for 10 minutes each in PBS with 0.1% Tween-20 (PBS-T), the membrane was incubated for 1 hour with diluted IRDye 680RD goat anti-rabbit IgG or IRDye 800CW goat anti-mouse IgG in Odyssey blocking buffer. The membrane was then washed three times for 10 minutes each in PBS-T and imaging using the Odyssey CLx imaging system. The membrane was probed again with mouse monoclonal anti-actin (Santa Cruz Biotech) or rabbit polyclonal anti-Actin (Cell Signaling Technology) for immunoblotting and imaging. In some experiments, the Coomassie blue stain was used (Bio-Rad, Hercules, CA, USA).

Example 7—Proteomics

For mass spectrometric protein identification, the appropriate bands were excised from protein gels and submitted for LC-MS/MS protein identification at the Donald Danforth Plant Science Center, Proteomics & Mass Spectrometry Facility (St. Louis, MO, USA). Samples were digested with trypsin and run on the LTQ-Orbitrap Velos using the 1-hour LC-MS/MS method.

All MS/MS samples were analyzed using Mascot (Matrix Science, London, UK; version 2.4.1. Mascot was set to search the cRAP_20 110301 database and NCBInr database (selected for Mus musculus, 174101 entries), assuming the digestion enzyme to be trypsin. Mascot was searched with a fragment ion mass tolerance of 0.80 Da and a parent ion tolerance of 15 ppm. Deamidated asparagine and glutamine, oxidation of methionine, and carbamidomethyl of cysteine were specified in Mascot as variable modifications.

Scaffold (version Scaffold_4.3.4, Proteome Software Inc., Portland, OR, USA) validated MS/MS-based peptide and protein identifications. Peptide identifications were accepted if they could be established at greater than 80.0% probability by the Scaffold Local FDR algorithm. Protein identifications were accepted if they could be established at greater than 99.0% probability and contained at least two identified peptides.

Protein probabilities were assigned by the Protein Prophet algorithm (Nesvizhskii et al., Anal. Chem. 2003; 75(17): 4646-58). Proteins that contained similar peptides and could not be differentiated based on MS/MS analysis alone were grouped to satisfy parsimony. Proteins sharing significant peptide evidence were grouped into clusters.

In general, cultured cancer cells were grown and incubated with the indicated amount of probe in Lab-Tek 8-chambered slides for the indicated time durations. Cells were washed with PBS at selected time points and underwent conventional slide preparation, ICC if indicated, and viewing under epifluorescence or confocal. For live-cell imaging of LS301, internalization at 37° C. in human dermal fibroblasts (Coriell Cell Technologies) and tumor cells including 4T1luc, MDA-MB-231, 5TGM, A549, and HL60 (ATCC) cells were cultured in appropriate media supplemented with 10% PBS and penicillin/streptomycin and incubated at 37° C. in 5% $CO_2$ incubator. The cells were grown on Lab-Tek 8-chamber slides (Nunc Inc. Rochester, NY) in the culture medium overnight before the experiment. The compounds were dissolved in 20% DMSO in 10 µM PBS (pH 7.4) (Sigma, St. Louis, MO) for stocking solution and mixed with culture medium to reach the final concentration. Cells were incubated with 1 µM compounds in chamber slides at different time points at 37° C. After LS301 treatment, the culture media was removed and followed by adding culture media containing SYTO 13 nuclear dye from (Thermo Fisher Scientific, Waltham, MA) for 45 minutes at 37° C. For assessing cellular colocalization of LS301 with lipid rafts, the Vybrant AlexaFluor 488 Lipid Raft Labeling Kit (Thermo Fisher Scientific, Waltham, MA, USA) was used per the manufacturer's instructions. Briefly, 4T1 cells were grown overnight in eight-chambered slides (ThermoFisher Scientific, Waltham, MA, USA) in phenol-free DMEM+10% FBS. LS301 was added to 4T1 cells at 5 µM for 1 hour, followed by staining with AlexaFluor 488-conjugated cholera toxin B for 10 minutes at 4° C., washing with PBS, and followed by adding anti-cholera toxin B antibody for 15 min at 4° C. to crosslink labeled lipid rafts and washing with PBS. Slides were mounted with Fluoromount-G mounting medium (Thermo-Fisher Scientific) before viewing. LS301 and AlexaFluor 488 fluorescence were imaged using the cypate filter set (Ex/Em 750-800 nm/818-873 nm) and fluorescein isothiocyanate (FITC) filter set (Ex/Em 460-500/510-560 nm), respectively.

For live-cell imaging of LS301 cell surface binding at 4° C., at first, the tumor cells and fibroblast cells were incubated with 1 µM of LS301 in culture medium for 1 hour at 4° C. in 35 mm glass-bottom culture dishes (MatTek Co., Ashland, MA, USA). In the 1.5 mL tubes, 1:250 monoclonal rabbit anti-ANXA2 antibody (Cell signaling Technology. Inc. Danvers, MA, USA) was incubated with 1:500 Alexa 488 anti-rabbit antibody (Thermo Fisher Scientific), and 1:250 mouse anti-pANXA2 antibody (Santa Cruz Biotechnology, Inc. Santa Cruz, CA) was incubated with 1:500 Alexa 546 donkey anti-mouse antibody (Thermo Fisher Scientific, Waltham, MA, USA) for 1 hour at 37° C. respectively. The cells treated with LS301 were washed twice and incubated with the first and second antibodies complexes for another hour at 4° C. Secondary antibody treatment alone served as controls. After washing twice, the cells were imaged using an FV1000 confocal microscope. FV1000 software determined the mean fluorescence intensities (Ex/Em=488/510-530 nm; Ex/Em=546/555-600 nm, 633/645-700 nm; Ex/Em 780/805-830 nm).

For LS301 cell internalization studies involving insulin treatment, cells were grown on Lab-Tek slides overnight. HEK 293T cells (or in some cases 4T1 cells) were maintained in DMEM medium supplemented with 10% fetal bovine serum and 100 units/mL penicillin. After DNA transfection, the HEK 293TAnxa2-WT-GFP and HEK 293TAnxa2-Y23A-GFP cells were maintained in Dulbecco's Modified Eagle's medium (DMEM) medium with 500 µg/mL G418, 10% fetal bovine serum (FBS), and 100 units/mL penicillin. The medium was changed, and cells were grown in serum-starved conditions overnight. Cells were then cultivated with or without 100 nM insulin for 4 h. Then 1 µM of LS301 was added to each sample to incubated for 4 hours or 24 hours at 37° C. Cells were imaged using an FV1000 confocal microscope, and the mean fluorescence intensities (Ex/Em=488/495 nm; Ex/Em=590/617 nm; Ex/Em=780/805-830 nm) were determined using the FV1000 software.

For Western blot analysis of insulin/PP2-induced change in cellular pANXA2 levels, 4T1 cells were treated with insulin or PP2 as above, lysed, and subjected to SDS-PAGE analysis. For mechanistic LS301 cell internalization experiments with endocytosis pathway inhibitors, 4T1 murine breast cancer cells were seeded in an 8-well plate at a density of 5000 cells/well with DMEM media supplemented with 10% FBS and penicillin/streptomycin and incubated overnight at 37° C. The next day, culture media was removed, followed by pre-treatment of cells with chlorpromazine hydrochloride at 13 µg/mL for 30 min, filipin complex at 3.2 µg/mL for 1 hour, or amiloride hydrochloride at 300 µM for 1 hour in a 300-µL volume of cell culture media. Next, the drug-containing media was removed after incubation and replaced with fresh culture media containing 6 µM or 0.9 µg/mL of LS301 in complete DMEM for 1 hour at 37° C.

For Pitstop 2 studies, 4T1 cells were incubated with Pitstop 2 reagent at 25 µM for 20 minutes, followed by incubation with LS301 at 2 µM for 1 or 3 hours. After LS301 treatment, the culture media was removed, followed by adding culture media containing SYTO 17 nuclear dye for 40 minutes at 37° C. Finally, nuclear stain media was removed. Cells were washed 2 times with PBS. They were later re-suspended in culture media for live-cell confocal microscopy imaging using Ex/Em=780/805-830 nm for LS301 and Ex/Em=621/634 nm for SYTO 17. ImageJ software corrected total cell fluorescence (CTCF) value from multiple cells per condition and summarized data with a box plot. Background signal was maintained at zero background for the analysis.

For LS301 intracellular trafficking experiments, 4T1 cells were cultured overnight using similar parameters as above. The next day culture media was removed, followed by incubation of cells with 200 µL of 4 µM LS301 in complete culture media for 5 hours at 37° C. At the end of this internalization process, LS301-containing media was removed, followed by three PBS washes. Fluorescence organelle staining and imaging were performed per manufacturers' protocols using VectaCell Rhodamine 123 for mitochondria, Lysotracker for lysosomes, BODIPY TR Ceramide for Golgi apparatus and CellLight Peroxisome-GFP, BacMam 2.0 for peroxisomes.

Immunocytochemistry was performed with 4% paraformaldehyde fixation, permeabilization with 0.1% Triton X-100 solution, and blocking with 5% normal goat serum and 1% BSA in 1×PBS blocking solution. Primary monoclonal antibodies against Rab5 (1:333) for early endosomes and Rab7 (1:333) for late endosomes were added to cells overnight at 4° C. The next day, wells were washed three times in PBS and then incubated with secondary Ab (goat anti-rabbit Dylight 550 nm (1:500)) for 1 hour. Finally, wells were washed three times and then imaged without coverslipping with a water immersion lens at 60×. ImageJ performed colocalization analyses to obtain the Pearson's correlation coefficient (PCC) and the scatterplot inset.

For in vitro blocking studies of LS301, 4T1 luc/GFP cells were treated for 24 h with LS301 alone, blocking peptide LCKLSL plus LS301, scrambled blocking peptide LGKLSL plus LS301, or unlabeled LS301 analog LS637 plus LS301. Cells were prepared for confocal microscopy.

For co-culture experiments on intercellular pANXA2/ANXA2 transfer, fibroblasts (FB) ($5 \times 10^4$ cells/well) were seeded on a 35-mm glass-bottom Petri dish (MarTek Cor. Ashland, MA, USA) overnight before seeding of $5 \times 10^4$ of cancer cells and further culture overnight before the experiment. LS301 (1 µM) was incubated with co-cultures of FB and ANXA2-YFP transfected HL60 cells, co-cultures of FB and wild-type HL60 cells, or co-cultures of FB and 4T1-GFP cells at 37° C. for 3 hours and then washed twice with 0.01 M PBS (pH 7.4). Then, the cells were fixed with 4% paraformaldehyde for 10 minutes.

For immunocytochemistry, slides were blocked with appropriate serum for 35 minutes or 5% non-fat milk PBS (pH 7.4) overnight at 4° C. Then, the slides were incubated with 1:500 monoclonal rabbit anti-ANXA2 antibody (Cell signaling Technology. Inc. Danvers, MA, USA), 1:500 monoclonal mouse anti-pANXA2 antibody (Santa Cruz Biotechnology, Inc. Santa Cruz, CA, USA), and/or 1:250 monoclonal mouse anti-vimentin antibody (Santa Cruz Biotechnology, Santa Cruz, CA, USA) for 1 hour at 37° C. After washing twice with PBS, the tissue sections were incubated with 1:1000 Alexa 488 anti-rabbit antibody (Thermo Fisher Scientific, Waltham, MA) and/or 1: 1000 TRITC labeled donkey anti-mouse IgG in MPBS (Jackson ImmunoResearch Lab, West Grove, PA, USA), for 1 hour at 25° C. Finally, slides were imaged under a confocal microscope as described in the Fluorescence Microscopy methods section. Fluorescence microscopy was performed using either an Olympus FV1000 confocal microscope (Olympus Corp., Tokyo, Japan) with filters/channels as follows: Ex/Em=488/510-530 nm; Ex/Em=546/555-600 nm, 633/645-700 nm; Ex/Em=785-825 nm/805-830 nm; or epifluorescence microscope with filters/channels as follows: 4',6-diamidino-2-phenylindole, (DAPI, Ex/Em=330-385/420 nm), FITC (Ex/Em=460-500/510-560 nm), Texas Red (Ex/Em=542-582/604-644 nm), and cypate (Ex/Em=750-800/818-873 nm), using exposure times 1 to 30 seconds and sensitivity settings ISO200-ISO1600. The same parameters were used for control and treatment groups unless otherwise indicated. ImageJ software (National Institutes of Health, Bethesda, MD, USA) was used for image processing.

In general, cells were fixed in Lab-Tek 8-chamber slides with 3% paraformaldehyde in PBS solution for 15 minutes. Nonspecific binding sites were blocked by PBS containing 10% donkey serum (blocking solution) for 1 hour. Cells were incubated overnight at 4° C. with the appropriate primary antibodies after three 5-minute PBS washes. Cells were then incubated at room temperature for 1 hour with diluted secondary donkey anti-rabbit antibody (Alexa Fluor 594) in blocking solution. Slides were counterstained and mounted with coverslips for imaging on an FV1000 confocal microscope. Mean fluorescence intensities (Ex/Em=590/617 nm) on the slide were determined using the FV1000 software. Cell transfection and transduction ANXA2-YFP expressing HL60 cells were generated by lentiviral transduction as follows. Human full-length ANXA2 cDNA in the pCMV6-AC-GFP vector was purchased from OriGene Technologies (Rockville, MD, USA). BamHI, XhoI, and AgeI restriction enzymes and Quick Ligation kit were purchased from New England Biolabs (Ipswich, MA, USA). An FCIV lentiviral vector containing IRES-Venus YFP under the ubiquitin promoter was obtained as a generous gift from Dr. Mingjie Lee at the Hope Center, Washington University School of Medicine (St Louis, MO, USA). The ANXA2 cDNA was subcloned into the FCIV lentiviral vector by restriction digest of the ANXA2 cDNA vector with BamHI and XhoI enzymes, restriction digest of the FCIV vector with BamHI and AgeI enzymes, and ligation using Quick Ligation per manufacturer's instructions. Klenow fragment and dNTP nucleotide mix (New England Biolabs) was used to fill sticky ends.

HEK 293T cells (ATCC) were cultured overnight in DMEM with 10% fetal bovine serum, 100 units/mL penicillin 100 μg/mL, streptomycin before transfection. DNA constructs were transfected into HEK 293T cells using Genejuice (EMD Millipore, Burlington, MA) per manufacturer's instructions. Culture supernatants were collected 40 hours after transfection, mixed 1:1 with Iscove's Modified Dulbecco's medium (IMDM) (Thermo Fisher Scientific) supplemented with 10% fetal bovine serum (FBS) and 1% Streptomycin, and added to HL60 cells in 6-well plates. At 72 hours post-transduction, the HL60 cells were checked under a confocal microscope for fluorescence. Populations of HL60 cells strongly expressing ANXA2-YFP were analyzed and collected by flow cytometry using a BD FACS AriaII Cell Sorter at a core laboratory at Washington University in St. Louis School of Medicine (St. Louis, MO, USA). Cell viability was checked by luciferase MTS assay as described in the MTS Assay section of methods. Transwell culture and extracellular vesicle transfer studies For transwell studies, human dermal fibroblasts (300,000 cells/well) were cultured alone in 6-well plates, or transwell with 4T1 cells (100,000 cells/insert) suspended within transwell inserts (3 μm pore polycarbonate membrane, MilliporeSigma, St. Louis, MO, USA). Cells were plated and grown in extracellular vesicle-depleted media for 72 hours and subsequently stained for pANXA2 using rabbit anti-pANXA2 primary antibody (15 min. at 4° C.) and donkey anti-rabbit AlexaFluor 594 conjugated secondary antibody (15 min. at 4° C.) at 1:500 dilutions, and visualized by fluorescence microscopy using the Texas Red filter set (Ex/Em=542-582/604-644 nm).

Extracellular vesicle-depleted media were generated by collecting flow-through after centrifugal filtration of complete DMEM media using Amicon Ultra-100K (100 kDa molecular weight cutoff membrane) devices (MilliporeSigma, St. Louis, MO). For extracellular vesicle transfer studies, supernatants from 4T1 cells cultured in extracellular vesicle-depleted media for 16 hours were harvested. The 4T1-derived extracellular vesicle fraction was concentrated by serial centrifugal filtration on Amicon Ultra-100K devices. The 4T1-derived extracellular vesicle fraction was then added to fibroblasts (60 μg/well) for 24 h, with untreated fibroblasts as control. LS301 was then added at 5 μM for 1 hour, and LS301 uptake was visualized by fluorescent microscopy using the cypate filter set (Ex/Em 750-800 nm/818-873 nm). A separate group of fibroblasts with or without added 4T1-derived extracellular vesicles was stained for pANXA2 using rabbit anti-pANXA2 primary antibody and donkey anti-rabbit AlexaFluor 594 conjugated secondary antibody at 1:500 dilutions and visualized by fluorescence microscopy as above.

For the MTS Assay, 6,000 4T1 or fibroblast cells (n=3) were seeded in 96-well plates and cultured in DMEM with 10% FBS at 37° C. overnight before treatment with different concentrations of LS301 for 48 hours or 72 hours. Cell viability was evaluated using CellTiterGlo Luminescent cell viability assay (Promega, USA) per manufacturer's instructions by standard plate reader for luminescence. The luminescence intensity from cells was normalized to reagent alone.

Overnight cultured 4T1 tumor cells in 96-well plates were treated with 0.5 μg/ml of doxorubicin (DOX) for 3 hours as a positive control. After treatment with different concentrations of LS30 for 48 hours or 72 hours, the cells were trypsinized, centrifuged, and washed twice with PBS (pH 7.4) before cell cytometry. Apoptotic cell death was determined using the FITC Annexin V Apoptosis Detection kit (Biolegend, USA) per manufacturer's instructions. Data were acquired and analyzed using BD FACS AriaII Cell Sorter (Beckman Coulter, USA) at the core laboratory at Washington University in St. Louis School of Medicine.

Example 8—Tissue Analysis

In general, tissues of interest were harvested and frozen at −80° C. in Optimal Cutting Temperature (OCT) media (storage at ≤−20° C.). Frozen sections were cut at 10-μm thickness, and slides were stored at −40° C. The LS301 fluorescence signal was then assessed by fluorescence microscopy using Cy7 filters or confocal microscope. Sections were subsequently fixed with 4% paraformaldehyde for 10 minutes.

For immunohistochemistry, slides were blocked with appropriate serum for 35 minutes or with 5% non-fat, milk PBS pH 7.4) overnight at 4° C. and incubated with primary antibody overnight at 4° C. or 1 hour at 37° C. For ANXA2/pANXA2 studies, tissue sections were incubated with 1:250 monoclonal rabbit anti-ANXA2 antibody (Cell signaling Technology, Inc. Danvers, MA) or 1:250 monoclonal mouse anti-pANXA2 antibody (Santa Cruz Biotechnology, Inc. Santa Cruz, CA). After washing twice with PBS, the tissue sections were incubated with 1:1000 AlexaFluor 488 anti-rabbit antibody (Thermo Fisher Scientific, Waltham, MA) and 1:800 TRITC labeled donkey anti-mouse IgG in MPBS (Jackson ImmunoResearch Lab, West Grove, PA, USA) for 1 hour at 25° C. respectively, Slides were washed again and stained with Hoechst or DAPI nuclear stains for 5 min or stained with 1:4000 nucleus dye ToPro3 (Thermo Fisher Scientific, Waltham, MA) for 45 minutes at 37° C. After final washes, a coverslip with aqueous fluorescence-saving mounting media was applied before imaging. Images were co-registered with others from the same sections to allow co-localization analysis.

For H&E staining, the same section or an adjacent frozen section was fixed for 10 min in 4% paraformaldehyde solution (Sigma, St. Louis, MO, USA) and stained with Harris hematoxylin for 90 seconds and with eosin (Sigma, St. Louis, MO) for 15 seconds, and then washed with tap water for 5 min. The tissue sections were mounted with Richard-Allan Scientific mounting medium (Thermo Fisher Scientific) and coverslips for microscopic examination.

For Z-stack imaging, the frozen 4T1 tumor tissue sections (10 μm thickness) were warmed in PBS (pH 7.4) for 5 min and then stained with SYTO-13 green fluorescent nuclear stain (Thermo Fisher Scientific, Waltham, MA) for 45 min at 37° C. Slides were imaged under a confocal microscope at Ex/Em=488/510-530 nm for SYTO-13 and Ex/Em=780/805-830 nm for detection of LS301. Each step of the Z-stack imaging ranged from 0.8 μm to 1.6 μm.

For quantitative correlation of pANXA2 expression to LS301 fluorescence in 4T1 luc-GFP, HT1080, and BxPC-3 tumors, the ImageJ plugin Colocalization Finder was applied to three representative tumor areas for each tumor type and determined the Pearson's correlation coefficients for pANXA2/LS301 signal overlap. For quantitative analysis of pANXA2 or ANXA2 signal within human tissues, FV1000 software was applied to calculate the fluorescence intensity at different areas in tumor tissues (n=3 mice/group, n=15 view spots), Ten lines were drawn in each view site, three view sites were chosen in tissue sections using 1.0× and 60× objective lens to do quantitative analysis. All values are the mean+ S.D., and Student's two-tailed unpaired t-test compared the difference. $P<0.05$ was accepted as statistically different.

For quantitative analysis of intratumoral LS301 levels in 4T1 luc/GFP, HT1080, and BxPC-3 tumors, mean fluorescence was measured for six independent views, including peripheral and core tumor tissues for each tumor type using ImageJ software (Analysis>Measure function). For quantitation of intratumoral distribution (periphery vs. core) of LS301 in 4T1 luc/GFP tumors, mean fluorescence was measured for three independent views of peripheral tumor tissues versus three independent views of core tumor tissues using ImageJ.

To establish the various tumor models, nude, Balb/c, or C57BL6 mice were injected with $10^5$-$10^7$ tumor cells subcutaneously on unilateral or bilateral flanks. In some cases, spontaneous tumor models were used. Animals injected subcutaneously with saline served as sham tumor controls. For near-infrared imaging, 100 μL volumes of 60 μM LS301 or cypate in PBS were injected intravenously by lateral tail vein, and animals were imaged using a Pearl Small Animal Imager (LI-COR Biotechnology, Lincoln, NE, USA) at the indicated time points. In some experiments, probes were formulated in 1% albumin in PBS. Animals were shaved using commercially available hair removal equipment and products before imaging. For experiments involving further tissue analysis, animals were anesthetized with isoflurane and euthanized by cervical dislocation under anesthesia. Organs were harvested by surgical dissection. For quantitative organ biodistribution studies, individual regions of interest were drawn around each organ of interest, and fluorescence was quantified using the Pearl Small Animal Imager software.

For flow cytometric analysis of cells from LS301-labeled 4T1 tumor xenografts, after injecting LS301 into 4T1 luc/GFP tumor-bearing mice at the time points indicated, the mice were imaged, euthanized, and tumors were excised and kept at −80° C. until analysis. Tumors were thawed, cut into small pieces, and incubated in trypsin for 1 to 2 hours at 37° C. The tissue was dissociated and filtered with a 40-μm cell strainer tube (Falcon 352235) to collect the sample and washed with PBS (pH 7.4) three times and further centrifuged for collection. The cells were sorted using a BD FACS AriaII Cell Sorter at a core laboratory at Washington University in St. Louis School of Medicine (St. Louis, MO, USA). Untreated cells, cells treated with LS301 (4 μM for 24 h), wild-type 4T1 cells (without GFP)), and 4T1 luc/GFP cells were used for compensation and gating. The sorted cells were classified and collected in fresh IMDM supplemented with 10% FBS and 1% streptomycin.

Example 9—Fluorescence Imaging-Guided Surgical Margin Assessment

Three 6-week old Balb/c mice were implanted with 100.000 4T1-Luc/GFP murine breast cancer cells orthotopically in the mammary fat pad below the right front leg. Seven to ten days post-implantation, all three mice were injected with 100 μL of calcium-formulated LS301 (5 mM Ca/60 μM LS301) via tail vein injection. Twenty-four hours post-injection, these mice were subjected to image-guided surgery using the CancerVision™ Goggle (CVG) system.

Mice were maintained under anesthesia using a continuous 5% isoflurane gas inhalation. A midline incision was made from the sternum to the base of the right front leg to create a skin flap along the tumor guided by LS301 fluorescence visualized using the CVG. The skin flap was deflected to expose and resect the tumor under fluorescence guidance. The surgical bed was surveyed for residual fluorescence, and additional fluorescent tissue identified using the CVG was resected.

In vivo confirmatory closed-field fluorescence images were obtained using the Pearl small animal imaging system (Li-Cor Biosciences, Lincoln, NE, USA) to ensure no residual fluorescence was left behind. Additional in vivo validation of complete tumor resection was obtained using quantitative bioluminescence imaging using the IVIS imaging system (PerkinElmer, Waltham, MA, USA) after injecting the mice with luciferin intraperitoneally before the start of surgical resection. All resected tissues were embedded in Tissue-Tek OCT (Sakura Finetek, Torrance, CA, USA) and frozen for preservation. All preserved tissues were sectioned into 10 μM thick slices using a cryo-microtome and immediately mounted onto microscope slides. Consecutive tissue section slides were observed for LS301 fluorescence using the epifluorescence microscope (Olympus B61). These sections were then stained using hematoxylin and eosin to identify cancerous tissue and imaged under brightfield conditions using the epifluorescence microscope to find correspondence between the fluorescence and cancerous regions.

Fluorescence quantification of images obtained using the CVG was done using ImageJ. Tumor-to-background ratio (TBR) calculations and statistical analyses were done using Origin Pro 8.0 software (OriginLabs). Means and standard errors denoted TBR average values and errors, respectively. Paired student's t-tests compared the TBRs before and after tumor resection to measure complete tumor resection and lack of residual fluorescence in the surgical bed. A $p$-value$<0.05$ was statistically significant.

Example 10—In Vivo LS301-Doxorubicin Drug Conjugate Therapy

Athymic nude mice (n=3 per group) were subcutaneously implanted with HT1080 human fibrosarcoma cells. Tumor growth was measured by a caliper twice weekly. On days 8, 11, and 15 post tumor implantation, mice were intravenously injected with either control (no treatment), doxorubicin alone, or LS301-doxorubicin drug conjugate at a dose of 0.5 µmol/kg. Mice were euthanized when tumors reached 2 cm in diameter in any direction. Survival was plotted using Kaplan-Meier curves, and statistical significance was assessed by a Logrank test of untreated control vs. LS301-doxorubicin treatment.

Example 11—DMSO-Based Formulation

At room temperature (~25° C.), 200 µL of DMSO was added to 0.5 mg LS301 and vortexed for about 1 minute to homogenize. The solution was centrifuged to remove any non-dissolved components. The concentration was measured via absorbance.

Generally, solution concentrations ranged between 290 and 330 µM. This concentrated solution was diluted dropwise into 800 µL phosphate-buffered saline (PBS) calculated such that the final concentration was 60 µM LS301 and that the final concentration was 20% DMSO/80% PBS by volume ("20% DMSO").

Example 12—Ethanol-Based Formulation

A 1:1 PEG400/Ethanol solution (v/v) was prepared by mixing 4 mL of PEG400 and 4 mL of ethanol and vortexing at high speed for 1 minute. 200 µL of this 1:1 solution was added to about 0.5 mg of LS301 to produce a transparent solution (>300 µM). No precipitate was observed after centrifugation. The solution was then added dropwise to a PBS/Ethanol solution, such that the final solution had a concentration of 60 µM, 10% PEG400, 10% ethanol solution, 80% PBS ("1:1 PEG400/Ethanol").

Example 13—NIR Contrast Evaluation for DMSO and Ethanol-Based Formulations

LS301 exhibited variable contrast when placed in different media, with demonstrable significantly increased contrast in 20% PEG400 (contrast in vivo over time) and 3e (contrast ex vivo). LS301 cleared via renal and hepatic mechanisms.

LS301 placed in 20% PEG400 solutions demonstrated increased tumor uptake compared to renal or hepatic clearance. Compared to DMSO based solvents, all the ethanol-based solvents demonstrated a more rapid increase in bladder fluorescence in vivo, suggesting increased renal clearance by ethanol-based solvents. No difference in histology between the various solvents was seen.

Example 14—Performance Test of PEG/Ethanol Formulation in Different Tumor Models LS301's solubility in ethanol ranged near the cutoff for producing a 20% ethanol/PBS solution. Besides, although 20% PEG400+20% ethanol had a higher contrast than the other solvent basis, efforts were made to reduce the non-aqueous component and increase the ease in producing the stock solution. The 1:1 PEG400/ethanol solution could maintain stability up to about 1-to-16 dilution. In vivo, a screening test was done by IV injection of 60 µM solution into a Balb/c mouse with two 4T1luc tumors dorsally injected. The data demonstrated increased contrast compared to 20% DMSO. To confirm LS301's multitumor affinity in the new solvent, solutions were tested against HT1080, A431, and DBT tumor-bearing mice. LS301 in 20% 1:1 PEG400 demonstrates a tumor-to-muscle ratio of greater than 10-fold in all three models and visible over time and ex vivo studies.

Example 15—HSA/MSA Formulation

One percent human serum albumin (HSA) or mouse serum albumin (MSA) was prepared by diluting 100 mL 25% HSA to 2.5 L with sterile water or dissolving 1 g MSA in sterile water. One gram LS301 was suspended in 10 L of 1% HSA or 1% MSA solution. The solution vortexed on a shaker for 30 minutes. The resulting LS301-HSA or LS301-MSA formulation was sterile filtered through Steriflip™ filter. Aliquots of the filtered sample were taken. The concentration of LS301 and HSA or MSA was confirmed via absorbance. The sample vials containing filtered LS301-HSA or LS301-MSA formulation were placed on dry ice to quick-freeze the sample. The frozen sample vials were placed onto the lyophilizer's tray dryer, then loaded into the lyophilizer to dry overnight (at least 12 hours). After lyophilization, the sample vials were removed from the lyophilizer's tray dryer, then crimp sealed. The sample vials were labeled and stored at −20° C. The resulting vial comprised 2 mg active LS301 and about 100 mg of HSA or MSA. LS301-HSA or LS301-MSA lyophilized product was reconstituted by injecting 10 mL of saline into vials to form a 0.2 mg/mL injection solution.

LS301-HSA formulation was evaluated in multiple cancer models with an injection dose of 0.35 mg/kg. NIR fluorescent images were monitored over time to confirm tumor accumulation. Without wishing to be bound by theory, formulating LS301 improved uptake into cancer cells, which use albumin for energy and express cell surface receptors, such as secreted protein acidic and rich in cysteine (SPARC), to internalize the LS301-albumin complex.

Example 16—HSA/MSA Formulation with Metal Ions

Five mM of metal chloride (Na, K, Ca, Mg, Mn, Al) solutions were prepared. To the LS301-HSA or LS301-MSA lyophilized product, 10 mL of 5 mM metal chloride solution were added to reconstitute the solution, which was then incubated at room temperature for at least 10 minutes before administration.

In vitro cell internalization studies were performed on a 4T1/luc cancer cell lines with 1 µM LS301-MSA formulation comprising 5 mM metal ions. Fluorescent confocal images were taken over time to investigate the internalization pattern difference between different metal ions. Adding divalent ions enhanced cell uptake of LS301-MSA formulation, whereas trivalent ions inhibited the cell uptake of LS301-MSA formulation.

In vivo NIR fluorescent imaging showed biodistribution of the formulations in 4T1luc tumor mice. Like the in vitro study, LS301-MSA with divalent metal ions enhanced tumor accumulation in a shorter time and maintained good tumor retention.

A colorectal cancer mice model was dosed via oral gavage. Fluorescence imaging and histology analysis both proved LS301-MSA targeted cancer cells through the GI system.

Example 17—Pluronic Gel Formulation for Topical Application

To formulate LS301 in a sol-gel mixture for topical administration, Pluronic F-127 (1 g; Sigma Aldrich, St.

Louis, MO) was dissolved in phosphate-buffered saline (PBS) (10 mL; PBS) to obtain a 10% (w/v) stock solution. A solution of LS301 (0.5 mL; 60 µM) was dissolved in 10% w/v aqueous Pluronic solution to form the sol-gel system, which was stored on ice before administration to maintain its liquid state.

To evaluate the Pluronic gel-LS301 formulation's performance, a topical approach of the formulation in-vivo study was conducted using a colon cancer HT29 mice model. 10 µL of the Pluronic gel-LS301 formulation was applied to the skin where the tumor was located. In-vivo NIR fluorescent images were taken at different time points post-application.

Example 18—Thermal Sensitive Hydrogel Formulation for Topical Application

PLGA-b-PEG-b-PLGA triblock copolymers (1500:1000:1500, transition temperature ~30° C., 250 mg) dissolved in 1 mL of cold water (5° C.) were mixed with 44 µg of LS301 in 1 mL tert-butanol at 60° C. and lyophilized for 24 hours. The lyophilized cake was then rehydrated with 1 mL of cold DI water at 4° C. and gently stirred for at least 6 hours in the cold room at 300 rpm. The rehydrated solution was passed through a 0.2-µm regenerated cellulose filter to remove unincorporated precursors.

Example 19—Liposomal Formulation of LS301

General preparation used DPPC (1,2-dipalmitoyl-sn-glycero-3-phosphocholine), DSPE-PEG (1,2-distearoyl-sn-glycero-3-phosphoethanolamine-N-[amino(polyethylene glycol)-5000 amine) and cholesterol (phosphocholine 67.5%, PEGylated phosphocholine 2.5%, cholesterol 30%) for the liposome. Lipid stock solutions were prepared by dissolving each lipid in chloroform in different glass vials. Aliquots from the stock solutions were mixed in a different glass vial to give 2 mL of solution with 30 mM lipid concentration. LS301 (0.005 mmol %, 2.205 mg) was dissolved in 20 µL dimethyl sulfoxide (DMSO) and added to the 2 mL lipid mixture. The solvent from the lipid mixture was evaporated off with a nitrogen stream to obtain a lipid film. The lipid film was further dried under vacuum at −100 kPa for 2 hours. The lipid film was then hydrated with 2 mL 120 mM ammonium sulfate. The lipid suspension thus formed was shaken at 60° C. for 30 minutes, followed by freeze-though cycles.

This suspension was extruded through a 50-nm polycarbonate membrane to form liposomes, purified through size exclusion chromatography to remove any unbound LS301. LS301 containing liposomes were prepared by extrusion in total lipid concentration of 30 mM. Size analysis of the liposomal-LS301 showed that the particle is around 30 nm.

Components of the liposome can and will vary, depending on the application. Different phosphocholine class lipids, PEGylated derivatives of phosphatidylcholine class lipids and cholesterol was used in different ratios to form the main core of the liposome. The phosphocholine class lipids that were used comprised:
- 1,2-dipalmitoyl-sn-glycero-3-phosphocholine (DPPC);
- 1,2-didodecanoyl-sn-glycero-3-phosphocholine (DLPC);
- 1,2-dimyristoyl-sn-glycero-3-phosphocholine (DMPC);
- 1,2-distearoyl-sn-glycero-3-phosphocholine (DSPC);
- 1,2-dioleoyl-sn-glycero-3-phosphocholine (DOPC);
- 1,2-dimyristoyl-sn-glycero-3-phosphoethanolamine (DMPE);
- 1,2-dipalmitoyl-sn-glycero-3-phosphoethanolamine (DPPE);
- 1,2-dioleoyl-sn-glycero-3-phosphoethanolamine (DOPE);
- 1,2-dimyristoyl-sn-glycero-3-phosphate (DMPA);
- 1,2-dipalmitoyl-sn-glycero-3-phosphatidic acid (DPPA); and
- 1,2-dioleoyl-sn-glycero-3-phosphate.

The PEGylated phosphocholine class lipids used comprised:
- 1,2-distearoyl-sn-glycero-3-phosphoethanolamine-N-[amino(polyethylene glycol)-5000[DSPE-PEG (5000) Amine];
- 1,2-distearoyl-sn-glycero-3-phosphoethanolamine-N-[amino(polyethylene glycol)-2000 [DSPE-PEG (2000) Amine];
- 1,2-distearoyl-sn-glycero-3-phosphoethanolamine-N-[carboxy(polyethylene glycol)-5000 [DSPE-PEG (5000) carboxylic acid];
- 1,2-distearoyl-sn-glycero-3-phosphoethanolamine-N-[carboxy(polyethylene glycol)-2000 [DSPE-PEG (2000) carboxylic acid];
- 1,2-distearoyl-sn-glycero-3-phosphoethanolamine-N-[succinyl(polyethylene glycol)-5000 [DSPE-PEG (5000) succinyl];
- 1,2-distearoyl-sn-glycero-3-phosphoethanolamine-N-[succinyl(polyethylene glycol)-2000 [DSPE-PEG (2000) succinyl]; and
- 1,2-distearoyl-sn-glycero-3-phosphoethanolamine-N-[maleimide(polyethylene glycol)-5000 [DSPE-PEG (5000) maleimide].

In vivo performance of liposomal-LS301 formulation was investigated in a PyMT BO1 tumor-bearing C57/B6 mice. Ex-vivo fluorescence imaging of biodistribution showed excellent tumor uptake of LS301.

The preceding description is given for clearness of understanding only. No unnecessary limitations should be understood from it, as modifications within the disclosure scope may be apparent to those having ordinary skill in the art. Throughout the specification, where compositions are described as including components or materials, it is contemplated that the compositions can also consist essentially of, or consist of, any combination of the recited components or materials, unless described otherwise. Likewise, where methods are described as including steps, it is contemplated that the methods can also consist essentially of, or consist of, any combination of the recited steps, unless described otherwise. The disclosure illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described concerning embodiments, a person of ordinary skill in the art will readily appreciate that other ways of performing the acts for the methods may be used. For example, the order of various of the steps may be changed without departing from the scope or spirit of the method unless described otherwise. Also, some of the individual steps can be combined, omitted, or further subdivided into additional steps.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments of the chemical groups represented by the variables contained within the generic chemical formulae described herein are specifically embraced by the present invention just as if each combination was individually explicitly recited, to the extent that such combinations embrace stable compounds (i.e., compounds that can be isolated, characterized and tested for biological activity). Also, all subcombinations of the chemical groups listed in the embodiments describing such variables, as well as all subcombinations of uses and medical indications described herein, are specifically embraced by the present invention just as if each subcombination of chemical groups and subcombination of uses and medical indications was individually and explicitly recited herein.

All patents, publications, and references cited herein are fully incorporated by reference. In case of conflict between the present disclosure and incorporated patents, publications, and references, the present disclosure should control.

What is claimed is:

1. A pharmaceutical composition comprising an effective amount of a compound chosen from cypate-Cyclo(Cys-Gly-Arg-Asp-Ser-Pro-Cys)-Lys-OH (LS301), cypate-Cyclo(Cys-Gly-Arg-Asp-Ser-Pro-Cys)-Tyr-OH (LS838) and a pharmaceutically acceptable salt thereof, wherein each amino acid residue is independently in a D or L configuration; a divalent metal ion; and a pharmaceutically acceptable carrier.

2. The pharmaceutical composition of claim 1, wherein the divalent metal ion is chosen from $Ca^{2+}$, $Mg^{2+}$, and $Mn^{2+}$.

3. The pharmaceutical composition of claim 2, wherein the divalent metal ion is $Ca^{2+}$.

4. The pharmaceutical composition of claim 3, wherein the divalent metal ion is present at a concentration between 1 mM and 10 mM.

5. The pharmaceutical composition of claim 4, wherein the divalent metal ion is present at a concentration of about 5 mM.

6. The pharmaceutical composition of claim 1, wherein the cypate is

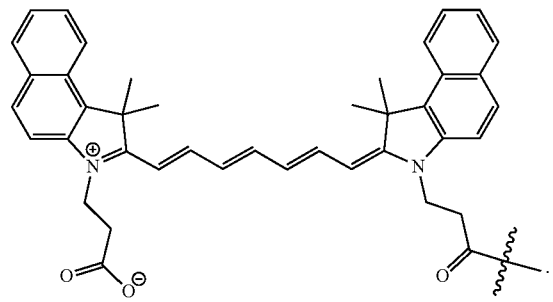 [SMILES: *C(=O)CCN1/C(=C/C=C/C=C/C=C/C2=[N+](CCC(=O)[O-])c3ccc4ccccc4c3C2(C)C)C(C)(C)c2c1ccc1ccccc21]

7. The pharmaceutical composition of claim 1, wherein at least one of the Cys amino acid residues is D-Cys.

8. The pharmaceutical composition to claim 1, wherein the compound is LS301 comprising the structural formula

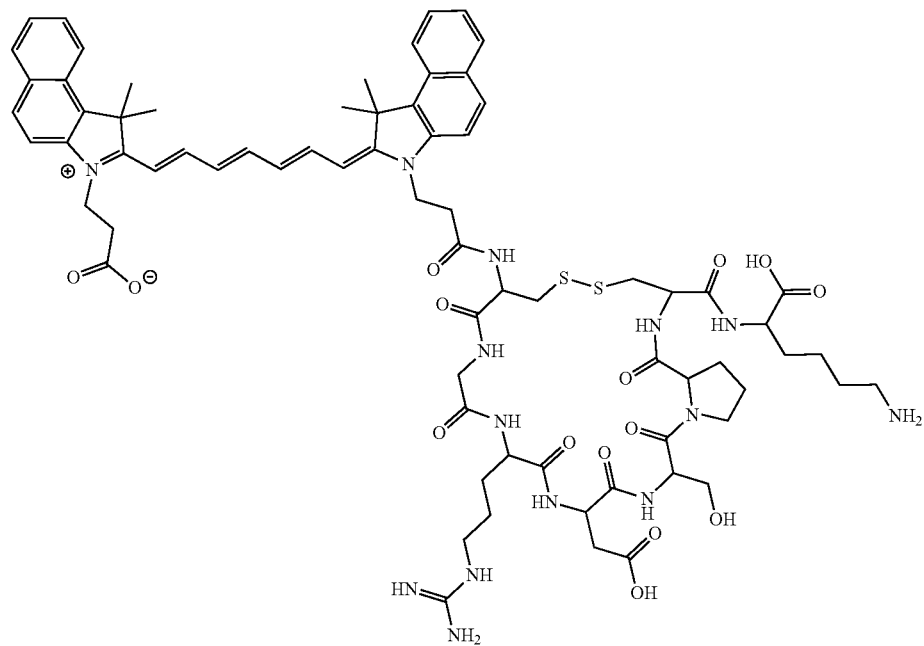 [SMILES: CC1(C)C(/C=C/C=C/C=C/C=C2/N(CCC(=O)NC3CSSCC(C(=O)NC(CCCCN)C(=O)O)NC(=O)C4CCCN4C(=O)C(CO)NC(=O)C(CC(=O)O)NC(=O)C(CCCNC(=N)N)NC(=O)CNC3=O)c3ccc4ccccc4c3C2(C)C)=[N+](CCC(=O)[O-])c2ccc3ccccc3c21]

or a pharmaceutically acceptable salt thereof.

9. The pharmaceutical composition to claim 8, wherein the compound is LS301 comprising the structural formula

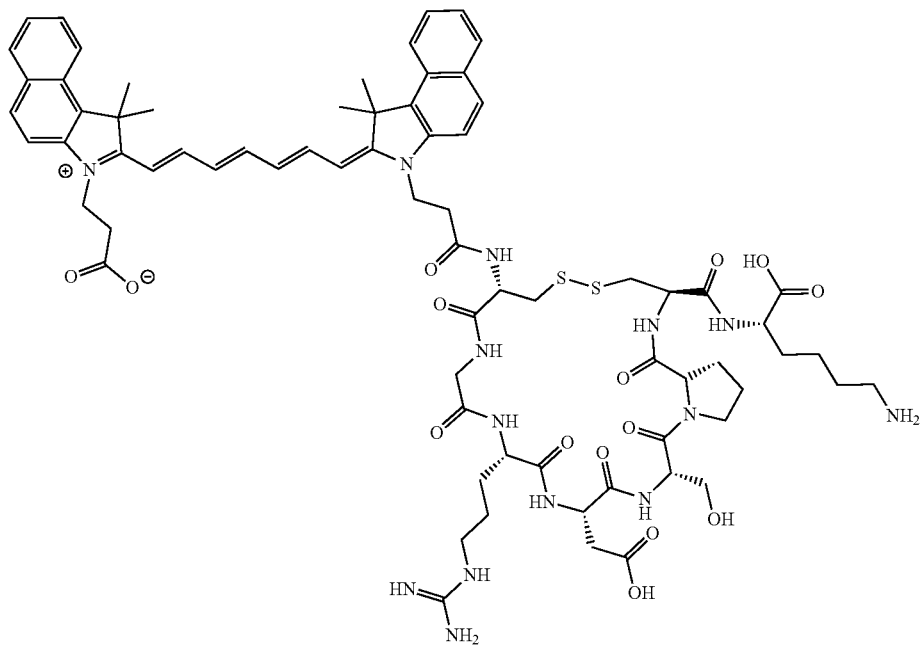
or a pharmaceutically acceptable salt thereof.
10. The pharmaceutical composition to claim 1, wherein the compound is LS838 comprising the structural formula
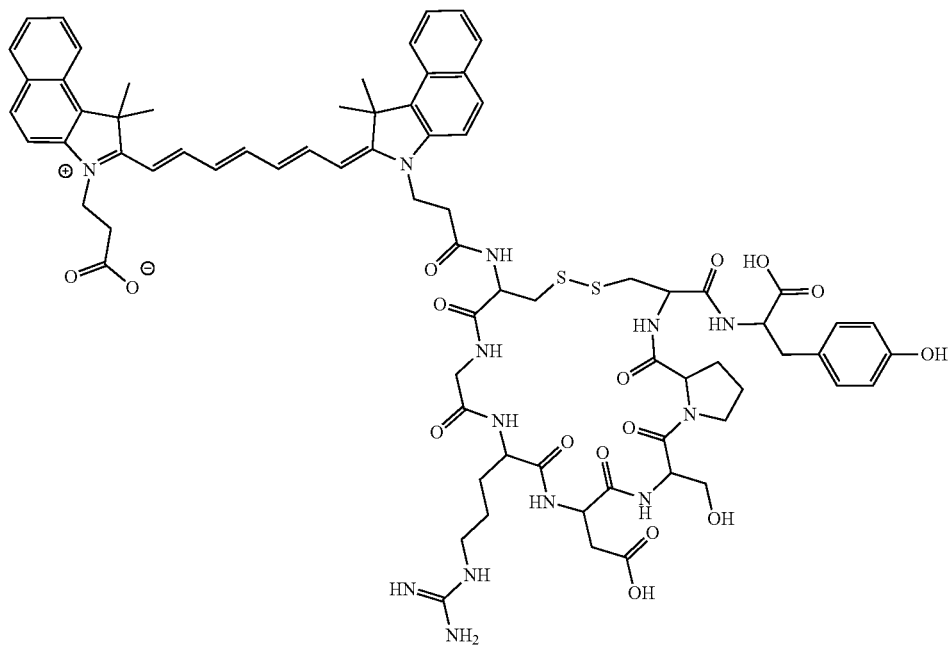 [SMILES: CC1(C)C(/C=C/C=C/C=C/C=C2/N(CCC(=O)NC3CSSCC(C(=O)NC(Cc4ccc(O)cc4)C(=O)O)NC(=O)C4CCCN4C(=O)C(CO)NC(=O)C(CC(=O)O)NC(=O)C(CCCNC(=N)N)NC(=O)CNC3=O)c3ccc4ccccc4c3C2(C)C)=[N+](CCC(=O)[O-])c2ccc3ccccc3c21]
or a pharmaceutically acceptable salt thereof.
11. The pharmaceutical composition of claim 9, wherein the compound is LS838 comprising the structural formula

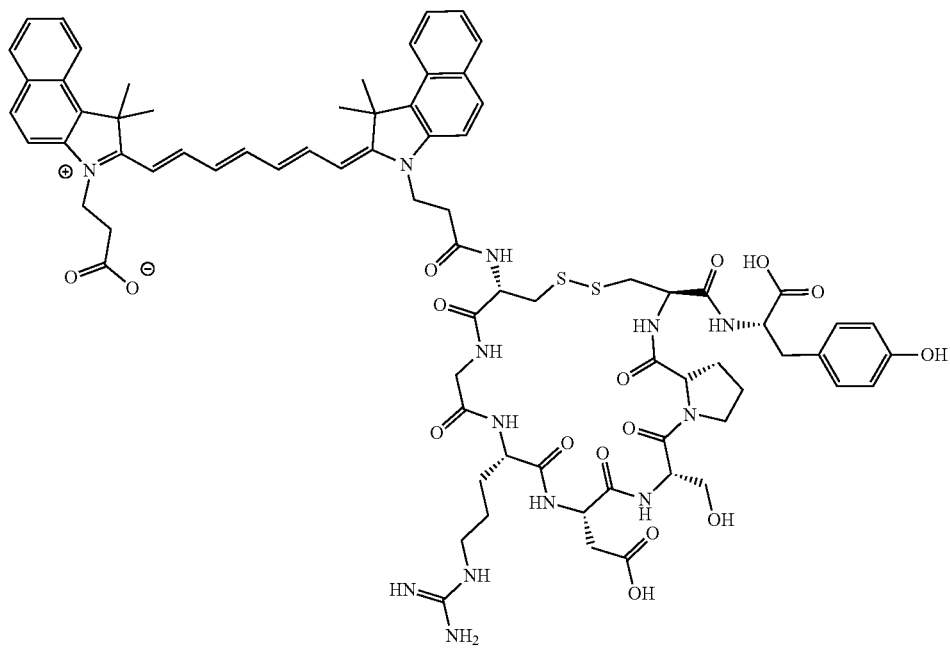

or a pharmaceutically acceptable salt thereof.

12. The pharmaceutical composition of claim 1, wherein the pharmaceutically acceptable carrier comprises phosphate-buffered saline.

13. The pharmaceutical composition of claim 1 formulated for intravenous administration.

14. The pharmaceutical composition of claim 1 formulated for topical administration.

15. The pharmaceutical composition of claim 1, wherein the effective amount is 0.2 µmol/kg.

16. The pharmaceutical composition of claim 1, wherein the effective amount is 0.4 µmol/kg.

17. The pharmaceutical composition of claim 1, wherein the effective amount is 0.6 µmol/kg.

18. A lyophilized product comprising:
a dye-conjugate chosen from cypate-Cyclo(Cys-Gly-Arg-Asp-Ser-Pro-Cys)-Lys-OH (LS301), cypate-Cyclo(Cys-Gly-Arg-Asp-Ser-Pro-Cys)-Tyr-OH (LS838) or pharmaceutically acceptable salts thereof, wherein each amino acid residue is independently in a D or L configuration, and a divalent metal ion.

19. The lyophilized product of claim 18, formed by a method comprising:
suspending the dye-conjugate in solution with the divalent metal ion;
mixing the suspension;
filtering the mixed suspension; and
lyophilizing the filtered suspension to form the lyophilized product.

20. The lyophilized product of claim 19, the dye-conjugate concentration in the suspension are measured via absorbance.

21. A vial comprising about 2 mg of the lyophilized product of claim 18.

22. An injectable solution comprising about 2 mg of the lyophilized product of claim 18 and about 10 mL of phosphate-buffered saline.

23. The injectable solution of claim 22, comprising about 0.2 mg/mL dye-conjugate.

24. A method of preparing an injectable solution, the method comprising mixing about 10 mL of phosphate-buffered saline into a vial comprising about 2 mg of the lyophilized product of claim 20 to form an injectable solution comprising about 0.2 mg/mL dye-conjugate.

25. A method for identifying compromised fibroblasts, comprising administering an effective amount of the pharmaceutical composition of claim 1 to a subject in need thereof.

26. The method of claim 25, wherein the compromised fibroblasts are proximal to dormant cancer cells.

27. The method of claim 26, wherein the dormant cancer cells are chosen from acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancer, brainstem glioma, brain tumors, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors, carcinoma of unknown primary, central nervous system lymphoma, cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, intraocular melanoma, retinoblastoma, gallbladder cancer, gastric cancer, gastrointestinal carcinoid tumor, gastrointestinal stromal tumor, germ cell tumors, gestational trophoblastic tumor, gliomas, gastric carcinoid, hairy cell leukemia, head and neck cancer, hepatocellular cancer, Hodgkin lymphoma, hypopharyngeal cancer, hypothalamic and visual pathway glioma, intraocular melanoma, islet cell carcinoma, Kaposi sarcoma, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, macroglobulinemia, malignant fibrous histiocytoma of bone/osteosarcoma, medulloblastoma, melanoma, intraocular melanoma, Merkel cell carcinoma, mesotheliomas, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, myeloid leukemias, multiple myeloma, myeloproliferative disorders, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia, pleuropulmonary blastoma, primary central nervous system lymphoma, prostate cancer, rectal cancer, renal cell carcinoma, renal pelvis and ureter transitional cell cancer, retinoblastoma, rhabdomyosarcoma, salivary gland cancer, sarcoma, Sézary syndrome, skin cancers, skin carcinoma, small cell lung cancer, small intestine cancer, soft tissue sarcoma, squamous cell carcinoma, squamous neck cancer with occult primary, stomach cancer, supratentorial primitive neuroectodermal tumor, T-Cell lymphoma, testicular cancer, throat cancer, thymoma, thymoma and thymic carcinoma, thyroid cancer, thyroid cancer, transitional cell cancer of the renal pelvis and ureter, trophoblastic tumor, unknown primary site, ureter and renal pelvis transitional cell cancer, urethral cancer, uterine cancer, uterine sarcoma, vaginal cancer, visual pathway and hypothalamic glioma, vulvar cancer, Waldenström macroglobulinemia, and Wilms tumor.

28. The method of claim 26, wherein the dormant cancer cells are pancreatic cancer.

29. The method of claim 26, wherein the pharmaceutical composition is administered intravenously.

30. The method of claim 26, wherein the pharmaceutical composition is administered topically.

31. The method of claim 30, wherein the topical administration is to the subject's colon.

32. A method of binding phosphorylated annexin A2 (pANXA2) protein in a biological sample comprising contacting the biological sample with a pharmaceutical composition of claim 1.

33. The method of claim 32, wherein the binding is selective over annexin A1 (ANXA1), non-activated ANXA2, and annexin A3 (ANXA3).

34. The method of claim 32, wherein tumor margins of cancer are defined.

35. The method of claim 32, wherein accuracy of cancer resection is improved during surgery.

36. The method of claim 32, wherein cancer is treated simultaneously from the periphery and interior core of a tumor.

37. The method of claim 36, wherein the cancer is chosen from acute lymphoblastic leukemia, acute myeloid leukemia, adrenocortical carcinoma, AIDS-related cancers, AIDS-related lymphoma, anal cancer, appendix cancer, astrocytoma, basal cell carcinoma, bile duct cancer, bladder cancer, bone cancer, brainstem glioma, brain tumor, ependymoma, medulloblastoma, supratentorial primitive neuroectodermal tumors, visual pathway and hypothalamic gliomas, breast cancer, bronchial adenomas/carcinoids, Burkitt lymphoma, carcinoid tumors, carcinoma of unknown primary, central nervous system lymphoma cerebellar astrocytoma, cerebral astrocytoma, malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, intraocular melanoma, retinoblastoma, gallbladder cancer, gastric cancer, gastrointestinal carcinoid tumor, gastrointestinal stromal tumor, germ cell tumors, gestational trophoblastic tumor, adult glioma, childhood brain stem glioma, childhood cerebral astrocytoma glioma, childhood visual pathway glioma, hypothalamic glioma, gastric carcinoid, hairy cell leukemia, head and neck cancer, hepatocellular cancer, Hodgkin lymphoma, hypopharyngeal cancer, hypothalamic and visual pathway glioma, intraocular melanoma, islet cell carcinoma, Kaposi sarcoma, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, macroglobulinemia, malignant fibrous histiocytoma of bone/osteosarcoma, medulloblastoma, melanoma, intraocular melanoma, Merkel cell carcinoma, mesotheliomas, metastatic squamous neck cancer with occult primary, mouth cancer, multiple endocrine neoplasia syndrome, multiple myeloma, plasma cell neoplasm, mycosis fungoides, myelodysplastic syndromes, myelodysplastic disease, myeloproliferative disease, myelogenous leukemia, myeloid leukemias, multiple myeloma, myeloproliferative disorders, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, plasma cell neoplasia, pleuropulmonary blastoma, primary central nervous system lymphoma, prostate cancer, rectal cancer, renal cell carcinoma, renal pelvis and ureter transitional cell cancer, retinoblastoma, rhabdomyosarcoma, salivary gland cancer, sarcoma, Sézary syndrome, skin cancers, skin carcinoma, small cell lung cancer, small intestine cancer, soft tissue sarcoma, squamous cell carcinoma, squamous neck cancer with occult primary, stomach cancer, supratentorial primitive neuroectodermal tumor, T-Cell lymphoma, testicular cancer, throat cancer, thymoma, thymoma and thymic carcinoma, thyroid cancer, thyroid cancer, transitional cell cancer of the renal pelvis and ureter, trophoblastic tumor, unknown primary site, ureter and renal pelvis transitional cell cancer, urethral cancer, uterine cancer, uterine sarcoma, vaginal cancer, visual pathway and hypothalamic glioma, vulvar cancer, Waldenström macroglobulinemia, and Wilms tumor.

* * * * *